(12) United States Patent
Wakasugi et al.

(10) Patent No.: US 10,366,785 B2
(45) Date of Patent: Jul. 30, 2019

(54) CONTROL METHOD, INFORMATION TERMINAL, RECORDING MEDIUM, AND DETERMINATION METHOD

(71) Applicant: Panasonic Intellectual Property Management Co., Ltd., Osaka (JP)

(72) Inventors: Kensuke Wakasugi, Tokyo (JP); Kenji Kondo, Ibaraki (JP); Kazutoyo Takata, Fukui (JP); Hirohiko Kimura, Fukui (JP); Toyohiko Sakai, Fukui (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 30 days.

(21) Appl. No.: 15/839,919

(22) Filed: Dec. 13, 2017

(65) Prior Publication Data

US 2018/0182481 A1    Jun. 28, 2018

(30) Foreign Application Priority Data

Dec. 22, 2016 (JP) .................................. 2016-248992

(51) Int. Cl.
*G16H 30/40* (2018.01)
*G06K 9/20* (2006.01)
(Continued)

(52) U.S. Cl.
CPC ........... *G16H 30/40* (2018.01); *G06K 9/2081* (2013.01); *G06K 9/3233* (2013.01); *G06K 9/342* (2013.01);
(Continued)

(58) Field of Classification Search
CPC ......... G06T 7/0012; G06T 2207/10081; G06T 2207/10116; G06T 2207/30096;
(Continued)

(56) References Cited

U.S. PATENT DOCUMENTS

2003/0210813 A1    11/2003 Oosawa
2006/0247525 A1*   11/2006 Huo ..................... G06T 7/0012
                                                                  600/437
(Continued)

FOREIGN PATENT DOCUMENTS

JP          4-052873        2/1992
JP          2003-210441     7/2003

OTHER PUBLICATIONS

Satoshi Suzuki et al., "Anaysis for Deep Convolutional Neural Network feature with Diffuse Lung Disease classification", IPSJ, vol. 2015-MPS-103 No. 29, Jun. 2015, pp. 1-6 (English Abstract).

(Continued)

*Primary Examiner* — Jingge Wu
(74) *Attorney, Agent, or Firm* — Wenderoth, Lind & Ponack, L.L.P.

(57) ABSTRACT

If a lesion included in a specification target image is a texture lesion, a probability image calculation unit calculates a probability value indicating a probability that each of a plurality of pixels of the specification target image is included in a lesion area. An output unit calculates, as a candidate area, an area including pixels whose probability values are equal to or larger than a first threshold in a probability image obtained from the probability image calculation unit and, as a modification area, an area including pixels whose probability values are within a certain probability range including the first threshold. An input unit detects an input from a user on a pixel in the modification area. A lesion area specification unit specifies a lesion area on the basis of the probability image, the candidate area, the modification area, and user operation information.

14 Claims, 17 Drawing Sheets

(51) Int. Cl.
*G06T 11/60* (2006.01)
*G06T 7/00* (2017.01)
*G06K 9/32* (2006.01)
*G06K 9/34* (2006.01)
*G06K 9/46* (2006.01)
*G06K 9/62* (2006.01)
*G06F 3/0484* (2013.01)
*G06F 16/583* (2019.01)

(52) U.S. Cl.
CPC ......... *G06K 9/4628* (2013.01); *G06K 9/4642* (2013.01); *G06K 9/4676* (2013.01); *G06K 9/627* (2013.01); *G06T 7/0012* (2013.01); *G06T 11/60* (2013.01); *G06F 3/04845* (2013.01); *G06F 16/583* (2019.01); *G06K 2209/05* (2013.01); *G06T 2200/24* (2013.01); *G06T 2207/10081* (2013.01); *G06T 2207/20076* (2013.01); *G06T 2207/20104* (2013.01); *G06T 2207/30061* (2013.01); *G06T 2207/30096* (2013.01); *G06T 2210/41* (2013.01)

(58) Field of Classification Search
CPC ............... G06T 7/136; G06T 7/143; G06T 2207/10132; G06T 2207/20036; G06T 2207/30004; G06T 5/002; G06T 11/60; G06T 2207/20076; G06T 2207/20081; G06T 2207/30048; G06T 2207/30061; G06T 2210/41; G06K 9/2081; G06K 9/3233; G06K 9/342; G06K 9/4628; G06K 9/4642; G06K 9/4676; G06K 9/627; G16H 30/40
See application file for complete search history.

(56) References Cited

U.S. PATENT DOCUMENTS

| | | | | |
|---|---|---|---|---|
| 2006/0257031 A1* | 11/2006 | Abramoff | ............ | G06K 9/6277 382/224 |
| 2008/0025592 A1* | 1/2008 | Jerebko | ................. | A61B 6/466 382/132 |
| 2009/0092300 A1* | 4/2009 | Jerebko | ................. | G06K 9/6278 382/128 |
| 2009/0202124 A1* | 8/2009 | Matsuda | ............... | G06T 7/0012 382/128 |
| 2010/0158332 A1* | 6/2010 | Rico | .................... | A61B 5/4312 382/128 |
| 2011/0216951 A1* | 9/2011 | Ye | .......................... | G06T 7/0012 382/128 |
| 2013/0322710 A1* | 12/2013 | Notte | ........................ | G06K 9/34 382/128 |
| 2014/0037170 A1 | 2/2014 | Sekiguchi et al. | | |
| 2014/0286551 A1 | 9/2014 | Yoshida et al. | | |
| 2015/0087982 A1* | 3/2015 | Mullick | .................... | G06T 7/41 600/443 |
| 2015/0302599 A1* | 10/2015 | Crainiceanu | .......... | G06T 7/0012 382/131 |
| 2016/0022238 A1* | 1/2016 | Park | ...................... | A61B 6/5217 600/410 |
| 2016/0117818 A1* | 4/2016 | Park | ....................... | G06T 7/0012 382/131 |
| 2016/0203589 A1* | 7/2016 | Dzyubak | ................. | G06T 5/002 382/131 |
| 2017/0161894 A1* | 6/2017 | Fisher | .................... | G06T 7/0012 |
| 2017/0337687 A1* | 11/2017 | Wang | ......................... | G06T 7/11 |
| 2018/0042567 A1* | 2/2018 | Smith | .................... | G06T 7/0016 |
| 2018/0122076 A1* | 5/2018 | Abedini | ................ | A61B 5/6898 |

OTHER PUBLICATIONS

Kazuki Kozuka et al., "Development of similar case retrieval technology for supporting medical image diagnosis and education of various lung diseases", IEICE, 113(410), Jan. 2014, pp. 139-142 (English Abstract).

* cited by examiner

CONTROL METHOD, INFORMATION TERMINAL, RECORDING MEDIUM, AND DETERMINATION METHOD

BACKGROUND

1. Technical Field

The present disclosure relates to a control method and the like for specifying a lesion area in a medical image, such as a magnetic resonance imaging (MRI) image or a computed tomography (CT) image.

2. Description of the Related Art

During these years, studies aiming to automatically detect lesion areas from medical images are taking place. In Japanese Patent No. 3046326, for example, a method for identifying a boundary of a lesion area using each of a plurality of pixels of a medical image and surrounding pixels and presenting a result of the identification as a candidate area for the lesion area is disclosed.

In addition, in Suzuki, Shouno, Kido, "Analysis for Deep Convolutional Neural Network Feature with Diffuse Lung Disease Classification", Technical Report, Mathematical Modeling and Problem Solving (MPS), 2015, 2015.29: 1-6, a deep learning technique, which has been producing excellent results in a field of image recognition, is applied to identification of lesions of diffuse lung diseases, and a technique for identifying a normal area and a plurality of types of lesion area is disclosed.

In Kazuki Kozuka, et. al, "Development of Similar Case Retrieval Technology for Supporting Medical Image Diagnosis and Education of Various Lung Diseases (Special Talk 1, Computer Assisted Diagnosis and Therapy Based on Computational Anatomy, etc.)", Institute of Electronics, Information and Communication Engineers (IEICE) Technical Report, Medical Images (MI), 2014, 113.410: 139-142, a system that retrieves similar images for twelve types of lesion is disclosed.

SUMMARY

A candidate area presented as a lesion area, however, might be deviated from an actual lesion area. In the above examples of the related art, no measures for correcting such a deviation through a simple operation are disclosed.

In the above examples of the related art, it is therefore difficult to efficiently determine a lesion area.

One non-limiting and exemplary embodiment provides a technique for efficiently determining a lesion area.

In one general aspect, the techniques disclosed here feature a method for controlling an information terminal including a display, the information terminal being connected to a case retrieval system that retrieves a medical image by referring to a medical image database. The method includes (a) receiving a first medical image including a plurality of pixels, (b) calculating, if a lesion included in the first medical image is a texture lesion, a probability value indicating a probability that each of the plurality of pixels of the first medical image is included in a lesion area by inputting a pixel value of the pixel and pixel values of surrounding pixels of the pixel to an identification device for identifying a predetermined lesion area indicating the texture lesion, the texture lesion being a lesion including one of a plurality of particular shadow patterns, (c) displaying, on the display, a second medical image obtained by superimposing a candidate area and a modification area of the candidate area upon the first medical image, the candidate area being determined on the basis of a pixel whose probability value is larger than a first threshold among the plurality of pixels, the modification area being determined on the basis of a pixel whose probability value is within a probability range among the plurality of pixels, the probability range including the first threshold, (d) detecting an input from a user on the second medical image displayed on the display, and (e) displaying a third medical image obtained by superimposing the lesion area upon the first medical image, the lesion area being determined by modifying the candidate area on the basis of the input from the user and the modification area.

According to the present disclosure, a lesion area can be efficiently determined.

It should be noted that this general or specific aspect may be implemented as an apparatus, a system, an integrated circuit, a computer program, a computer-readable recording medium, which may be a nonvolatile recording medium such as a compact disc read-only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
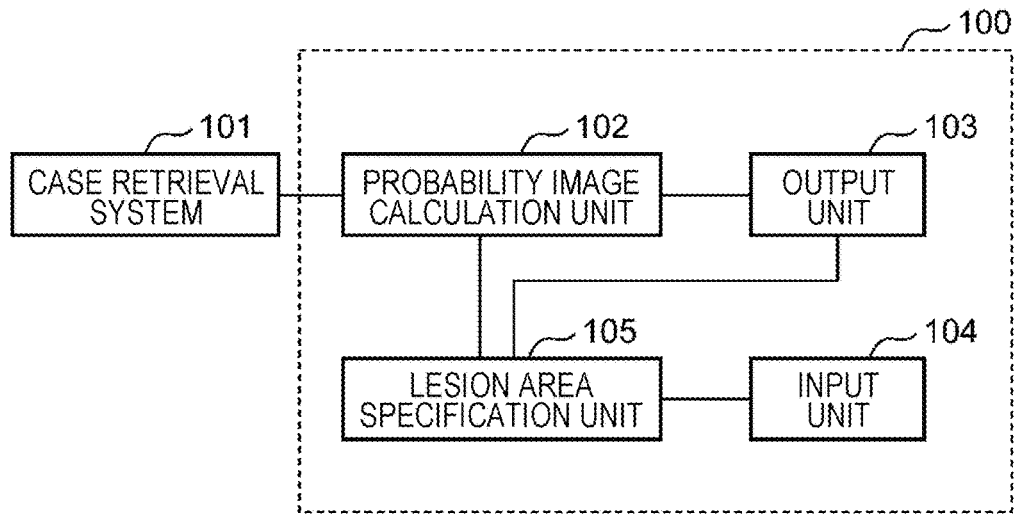
FIG. 1 is a block diagram illustrating the characteristic functional configuration of an information terminal according to a first embodiment of the present disclosure.

Underlying Knowledge Forming Basis of Present Disclosure

A large amount of medical images can now be easily accumulated as a result of recent digitization of medical images, and computer-aided diagnoses employing such data are enthusiastically studied and developed. One of the computer-aided diagnoses is automatic detection of lesion areas. When similar case retrieval is performed, for example, a lesion area used for the retrieval needs to be accurately specified, but it is difficult to accurately and promptly specify a lesion having a complex shape. By automatically detecting lesion areas, therefore, the lesion areas can be simply and accurately specified.

An example of the related art that provides a method for simply and accurately specifying a lesion area is Japanese Patent No. 3046326. In this example of the related art, a method for identifying a boundary of a lesion area using each of a plurality of pixels of a medical image and surrounding pixels and presenting a result of the identification as a candidate area for the lesion area is disclosed. A pixel and surrounding pixels thereof are collectively referred to as a "local area image", and the pixel is at the center of the local area image.

In addition, as a result of improvement in image recognition techniques, types of lesion included in local area images can now be identified as disclosed in Suzuki, Shouno, Kido, "Analysis for Deep Convolutional Neural Network Feature with Diffuse Lung Disease Classification", Technical Report, Mathematical Modeling and Problem Solving (MPS), 2015, 2015.29: 1-6. In this example of the related art, a deep learning technique, which has been producing excellent results in a field of image recognition, is applied to identification of lesions of diffuse lung diseases, and a normal area and a plurality of types of lesion are identified.

Whereas the deep learning technique usually requires a large amount of learning data, in Kazuki Kozuka, et. al, "Development of Similar Case Retrieval Technology for Supporting Medical Image Diagnosis and Education of Various Lung Diseases (Special Talk 1, Computer Assisted Diagnosis and Therapy Based on Computational Anatomy, etc.)", Institute of Electronics, Information and Communication Engineers (IEICE) Technical Report, Medical Images (MI), 2014, 113.410: 139-142, a large number of local area images are extracted from a single image to prepare a large amount of learning data, and then the deep learning technique is applied. By using this technique as an identification device that identifies which of a normal area and a lesion area a central pixel of a local area image is included, a lesion area can be automatically detected. That is, by presenting an automatically detected lesion area as a candidate area used by a doctor to specify a lesion area, an accurate lesion area might be set in a medical image through a simple operation.

If a lesion included in a local area image extracted from a medical image is identified and a lesion area is automatically detected using the result as in "Analysis for Deep Convolutional Neural Network Feature with Diffuse Lung Disease Classification", however, an appropriate candidate area might or might not be detected depending on a type of lesion. If an appropriate candidate area is detected, the work efficiency of specification of a lesion area improves, but if not, the work efficiency decreases. In this case, a deviation between a candidate area and an actual lesion area needs to be corrected, but in this example of the related art, measures for correcting such a deviation through a simple operation are not disclosed.

The technique disclosed in "Development of Similar Case Retrieval Technology for Supporting Medical Image Diagnosis and Education of Various Lung Diseases" is a technique for determining whether a medical image includes any of twelve types of lesion area, not a technique for extracting a candidate area for a lesion area from a medical image and correcting a deviation between the extracted candidate area and an actual lesion area through a simple operation.

Medical images include various lesions, and shapes and/or sizes of the lesions largely vary depending on a type of lesion, a course of a disease, and/or individual differences. In a lung CT image of a diffuse lung disease, one of several characteristic patterns or shapes, such as a honeycomb lung, a ground glass shadow, a granular shadow, a cavity nodule, and an infiltrative shadow, is observed. In "Analysis for Deep Convolutional Neural Network Feature with Diffuse Lung Disease Classification", a lesion is identified using a local area image of a predetermined size, and a lesion can be identified insofar as a pattern or a shape that can be used for the identification of the lesion is included in a local area image.

Figure 19:
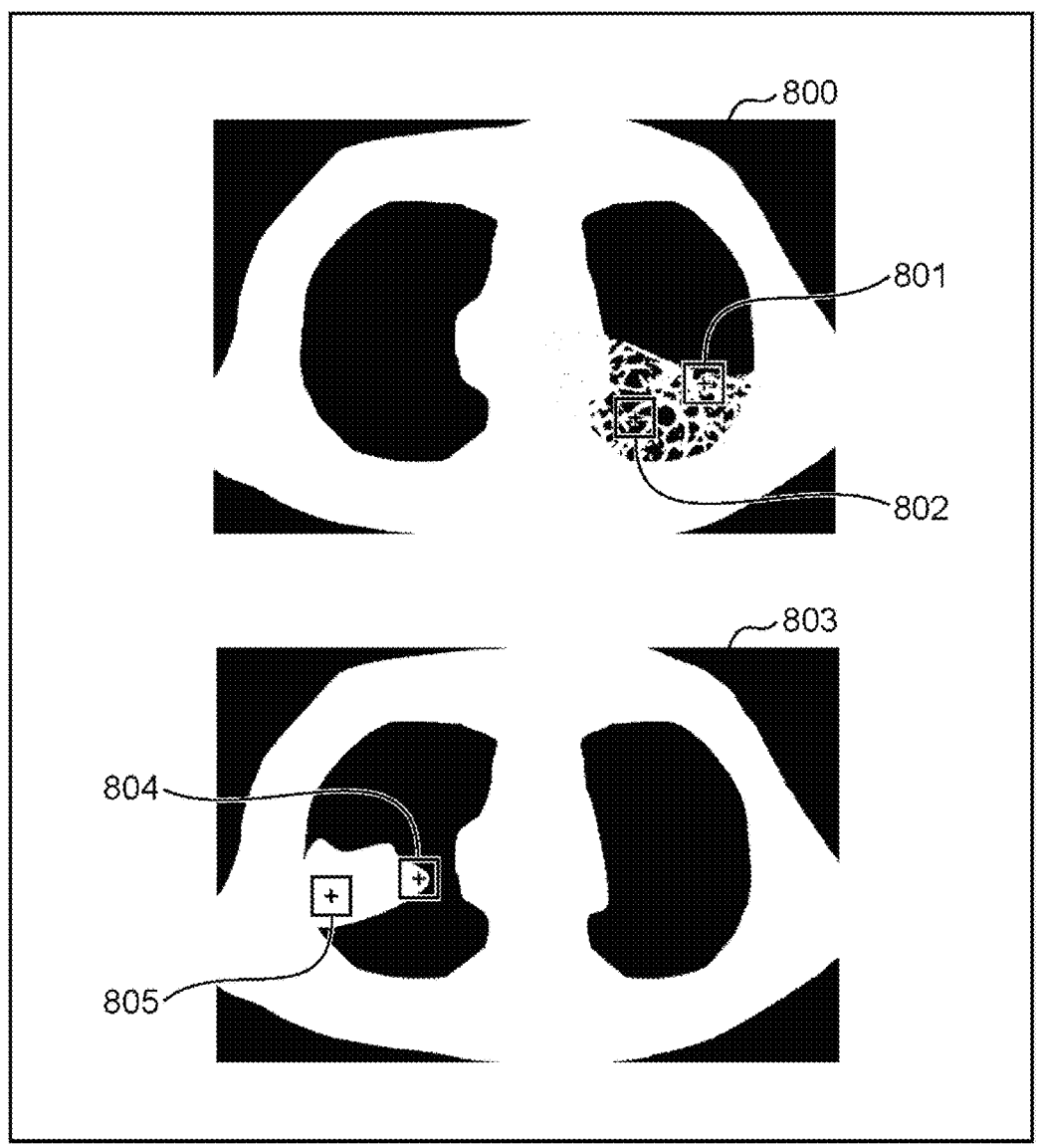
FIG. 19 is a diagram illustrating an example of a lung CT image including a honeycomb lung and a lung CT image including an infiltrative shadow.

FIG. 19 is a diagram illustrating an example of a lung CT image 800 including a honeycomb lung and a lung CT image 803 including an infiltrative shadow. In the lung CT image 800, a local area image 801 is extracted from around a boundary between a honeycomb lung area and a normal area. In the lung CT image 800, a local area image 802 is extracted from an area completely included in the honeycomb lung area.

In the lung CT image 803, a local area image 804 is extracted from around a boundary between an infiltrative shadow area and a normal area. A local area image 805 is extracted from an area completely included in the infiltrative shadow area.

Because a texture lesion such as a honeycomb lung, a ground glass shadow, or a granular shadow has a characteristic in a texture thereof, a local area image invariably includes a characteristic texture regardless of a position of a pixel included in a lesion area used as a central pixel to extract the local area image. A lesion area, therefore, can be automatically detected using a local area image.

In the case of a shape lesion such as a pustule, a cavity nodule, or an infiltrative shadow, on the other hand, a local area image extracted from a lesion area does not necessarily include a characteristic shape. It is assumed, for example, that an infiltrative shadow extends beyond a local area image. The local area image 804, which is extracted using a pixel near the boundary between the infiltrative shadow area and the normal area as a central pixel, includes a shape characteristic to an infiltrative shadow.

The local area image 805, which is extracted using a pixel at around the center of the infiltrative shadow area distant from the boundary between the infiltrative shadow area and the normal area as a central pixel, however, does not include a shape characteristic to an infiltrative shadow. An area at the center of the infiltrative shadow area, therefore, is not automatically detected as an infiltrative shadow area. In addition, in the case of a shape lesion, a local area image extracted from around a boundary between a lesion area and a normal area does not necessarily have a characteristic shape. If a lesion occurs near the chest wall, for example, a boundary between a lesion area and a normal area runs along the chest wall. As a result, a local area image extracted from around the boundary does not exhibit a characteristic shape, and automatic detection is difficult.

When a lesion area is automatically detected, therefore, a texture lesion area may be used.

The present disclosure has been established in view of these problems, and aims to provide a technique for efficiently determining a lesion area extracted from a medical image.

A method for controlling an information terminal according to an aspect of the present disclosure is a method for controlling an information terminal including a display, the information terminal being connected to a case retrieval system that retrieves a medical image by referring to a medical image database, the method including:

(a) receiving a first medical image including a plurality of pixels;

(b) calculating, if a lesion included in the first medical image is a texture lesion, a probability value indicating a probability that each of the plurality of pixels of the first medical image is included in a lesion area by inputting a pixel value of the pixel and pixel values of surrounding pixels of the pixel to an identification device for identifying a predetermined lesion area indicating a texture lesion, the texture lesion being a lesion including one of a plurality of particular shadow patterns;

(c) displaying, on the display, a second medical image obtained by superimposing a candidate area and a modification area of the candidate area upon the first medical image, the candidate area being determined on the basis of a pixel whose probability value is larger than a first threshold among the plurality of pixels, the modification area being determined on the basis of a pixel whose probability value is within a probability range among the plurality of pixels, the probability range including the first threshold;

(d) detecting an input from a user on the second medical image displayed on the display; and (e) displaying a third medical image obtained by superimposing the lesion area upon the first medical image, the lesion area being determined by modifying the candidate area on the basis of the input from the user and the modification area.

When a candidate area for a lesion area has been extracted from a medical image through image processing and presented, modification might be necessary. Because the periphery of a lesion area is complex in shape and extraction by an identification device is difficult, the periphery of a lesion area may be manually modified. A manual modification operation, however, is cumbersome.

In the present aspect, not only a candidate area including pixels whose probability values included in a texture lesion is equal to or larger than a first threshold but also a modification area including pixels whose probability values are within a probability range including the first threshold is superimposed upon a first medical image. As a result, an area to be modified becomes evident, and a modification operation can be performed efficiently. In addition, the modification area is determined on the basis of not a distance on an image but probability values. When a modification area has been determined on the basis of a distance on an image, it is difficult to distinguish a boundary line that does not require modification and a boundary line that requires modification, and the user needs to determine which boundary line is to be modified and finely modify the boundary line. Since a modification area is determined on the basis of probability values in the present aspect, a boundary line that requires modification can be clearly identified.

In addition, since a lesion area exhibiting a texture lesion including one of a plurality of particular shadow patterns is to be extracted, a lesion area can be extracted more accurately using an identification device than when a lesion area exhibiting a shape lesion is to be extracted. In the present aspect, therefore, a probability that a modification area indicates an area around a boundary of an actual lesion area increases, and the user can determine a lesion area through a simple operation. The user, therefore, can efficiently determine a lesion area.

In the above aspect, in (c), the modification area to be superimposed upon the second medical image may be divided into a plurality of sub-areas, and in each of the plurality of sub-areas, a longest straight line connecting two pixels selected from the sub-area may be equal to or shorter than a second threshold.

According to the present aspect, since the modification area is divided into a plurality of sub-areas, with each of which a longest straight line connecting two pixels is equal to or shorter than the second threshold, the user can perform an operation for correcting a deviation between a candidate area and an actual lesion area for each of the sub-areas. The user, therefore, can correct a deviation between a candidate area and an actual lesion area through a simple operation.

In the above aspect, in (d), an input from the user as to whether to add or exclude each of the plurality of sub-areas to or from the candidate area may be detected, and in (e), a candidate area determined on the basis of the input from the user may be displayed as the lesion area.

According to the present aspect, the user can determine a lesion area by performing a simple operation (e.g., a click operation) for determining, for each of the sub-areas, whether to add or exclude the sub-area to or from a candidate area.

In the above aspect, in (c), the modification area may be displayed such that the modification area includes the candidate area, in (d), an input from the user on a pixel included in the modification area may be detected, and in (e), the lesion area may be an area obtained by enlarging or reducing the candidate area on the basis of a part of the modification area in accordance with the input from the user.

When the entirety of a boundary line is modified, a plurality of operations need to be performed. If a boundary line is a polygon including a plurality of points extending in a circle shape, pixels included in the boundary line need to be adjusted in order to modify the boundary line.

In the present aspect, a boundary line of a modification area is calculated on the basis of an isopleth in a probability image, the user can automatically draw an isopleth passing through an arbitrary point in the modification area by specifying the point. In the present aspect, therefore, a boundary of a candidate area is replaced by an isopleth passing through a point at which the user has performed a click operation, and the user can modify the candidate area through the single click operation.

In the above aspect, in (e), a degree to which the candidate area is enlarged or reduced when an input from the user on a first pixel has been detected may be set lower than when an input from the user on a second pixel has been detected, and an inclination of probability values of surrounding pixels of the first pixel may be larger than an inclination of probability values of surrounding pixels of the second pixel.

When an operation for moving a boundary line to a desired position is performed to enlarge or reduce a candidate area, the user needs to accurately move a mouse. In addition, because an inclination of probability values is not visually observed on a medical image, it is difficult to predict the amount of change and, accordingly, perform modification. In the present aspect, when a candidate area is enlarged or reduced in accordance with the amount of drag, the amount of change is small in an area in which an inclination of probability values is large and large in an area in which an inclination of probability values is small. The user, therefore, can accurately adjust a candidate area in an area in which an inclination is large, where a drag operation needs to be accurately performed, and modify the candidate area accurately and simply. In an area in which an inclination is small, where a drag operation need not be accurately performed, on the other hand, the user can roughly adjust a candidate area and promptly determine the candidate area.

In the above aspect, in (d), a drag operation performed by the user may be detected as the input, and in (e), the first and second pixels may each be a pixel at a start point of the drag operation, and the degree to which the candidate area is enlarged or reduced may be proportional to an amount of movement in the drag operation and inversely proportional to the inclination.

According to the present aspect, since the degree to which a candidate area is enlarged or reduced becomes lower as an inclination of surrounding pixels of a pixel at a start point of a drag operation, a modification area can be finely modified in an area in which an accurate operation is required. In addition, since the degree to which a candidate area is enlarged or reduced is proportional to the amount of movement in a drag operation, the degree to which a candidate area is enlarged or reduced can be determined in consideration of the user's intuition.

A determination method according to an aspect of the present disclosure includes receiving a medical image including pixels, each of the pixels having a pixel value, calculating probability values each corresponding to the pixels, each of the probability values indicating a probability that a corresponding pixel is included in a lesion area, determining, from among a first area, a second area, a third area, and a fourth area, an area to which each of the pixels belongs, each of pixels included in the first area having a pixel value equal to or larger than an upper limit, each of pixels included in the second area having a pixel value equal to or larger than a first threshold but smaller than the upper limit, each of pixels included in the third area having a pixel value larger than a lower limit but smaller than the first threshold, each of pixels included in the fourth area having a pixel value equal to or smaller than the lower limit, the upper limit being larger than the first threshold, the first threshold being larger than the lower limit, receiving first selections of one or more areas included in the second area, determining one or more fifth areas being included in the second area and not being selected in the first selections, receiving second selections of one or more areas included in the third area, determining one or more sixth areas being included in the third area and being selected in the second selections, and determining pixels included in the first area, the one or more fifth areas, and the one or more sixth areas are included in the lesion area.

Advantageous effects produced by the above method can be produced by an information terminal and a program.

Embodiments

First, terms used in the following embodiments will be described.

A "probability image" refers to an image including, as a pixel value, a probability value indicating a probability that each of a plurality of pixels thereof is included in a lesion area.

A "texture lesion" refers to a lesion that repeatedly exhibits a particular shadow pattern.

A "non-texture lesion" refers to a lesion that is not classified as a texture lesion.

A "lesion area" refers to an area in a medical image determined by a doctor as a lesion area.

A "candidate area" refers to an area that has been calculated using one of methods according to the embodiments of the present disclosure and that is a candidate for a lesion area. That is, a "candidate area" refers to an area including pixels whose probability values, which will be described later, are equal to or larger than an upper limit of a probability range.

A "modification area" refers to an area that can be removed from or added to a candidate area.

A "specification target image" refers to an image in which a user, namely a doctor, for example, is to set a lesion area.

A "local area image" refers to an area of a particular size extracted from a medical image.

A "sub-area" refers to an area obtained by dividing a modification area in a particular manner.

A "largest inter-pixel distance and two end pixels" refer to, among all combinations of two peripheral pixels of a sub-area, two pixels with which a largest inter-pixel distance is obtained and the largest inter-pixel distance.

First Embodiment

Configuration

An information terminal according to a first embodiment of the present disclosure will be described in detail hereinafter with reference to the drawings.

In the following description, the lungs will be taken as an example of an imaging target, and CT images will be used as an example of medical images.

FIG. 1 is a block diagram illustrating the characteristic functional configuration of an information terminal 100 according to a first embodiment of the present disclosure.

Details of components of a case retrieval system 101 and the information terminal 100 illustrated in FIG. 1 will be described hereinafter.

The case retrieval system 101 transmits, to the information terminal 100, a medical image in which a lesion area is not specified. The case retrieval system 101 receives a medical image from the information terminal 100. The case retrieval system 101 stores a database of one or more cases including medical images to which diagnoses have been given. The case retrieval system 101 calculates image feature values between a received medical image and the medical images included in the database. The case retrieval system 101 then searches the database for a medical image having a certain degree of similarity to the received medical image to retrieve a case corresponding to the received medical image, and transmits case data regarding the retrieved case to the information terminal 100. Case data includes, for example, a found medical image and a diagnosis.

The database stored in the case retrieval system 101 includes medical images in which lesion areas are specified and medical images in which lesion areas are not specified. The database stored in the case retrieval system 101 also includes medical images including lesion areas indicating texture lesions and medical images including lesion areas indicating non-texture lesions.

The case retrieval system 101 is a computer including a processor such as a central processing unit (CPU), a read-only memory (ROM), a random-access memory (RAM), a nonvolatile storage device, and a communication device for communicating with the information terminal 100.

The information terminal 100 includes a probability image calculation unit 102, an output unit 103, an input unit 104, and a lesion area specification unit 105. The information terminal 100 is connected to the external case retrieval system 101. The information terminal 100 may be connected to the case retrieval system 101 through a public communication network such as the Internet or through a local area network. The information terminal 100 is a computer including a processor such as a CPU, a ROM, a RAM, a nonvolatile storage device, and a communication device for communicating with the case retrieval system 101. A display (not illustrated) and an operation device (not illustrated) are connected to the information terminal 100. The display is, for example, a liquid crystal display or an organic electroluminescent (EL) display. The operation device is, for example, a keyboard, a mouse, or a touch panel.

The probability image calculation unit 102 obtains, from the case retrieval system 101, a specification target image (an example of a first medical image), which is a medical image in which a lesion area is to be specified. A "lesion area" refers to an area in a specification target image determined by the user as a lesion area. A specification target image may be a CT image.

If a lesion included in a specification target image is a texture lesion, the probability image calculation unit 102 calculates a probability value indicating a probability that each pixel of the specification target image is included in a lesion area. An image having the calculated probability values as pixel values thereof are called a "probability image". The probability image calculation unit 102 includes identification devices for identifying predetermined lesion areas. The probability image calculation unit 102 sequentially sets a pixel in a specification target image as a central pixel and then sets an area including the central pixel and surrounding pixels around the central pixel as a local area image. The probability image calculation unit 102 then inputs pixel values of the pixels of the local area image to an identification device in order to calculate probability values relative to the central pixel. The probability image calculation unit 102 generates a probability image by performing the above process on all the pixels of the specification target image.

The probability image calculation unit 102 outputs the probability image and the specification target image to the output unit 103 and the probability image to the lesion area specification unit 105. A specific method for determining whether a lesion included in a specification target image is a texture lesion will be described later.

The output unit 103 calculates, in a probability image obtained from the probability image calculation unit 102, an area including pixels whose probability values are equal to or larger than a first threshold as a candidate area. The output unit 103 also calculates an area including pixels whose probability values are within a certain probability range including the first threshold as a modification area. The output unit 103 outputs the candidate area and the modification area to the lesion area specification unit 105. The output unit 103 also displays, on the display, a medical image (an example of a second medical image) obtained by superimposing the candidate area and the modification area upon a specification target image obtained from the probability image calculation unit 102. A specific method for calculating a modification area will be described later. As a method for superimposing a candidate area and a modification area upon a specification target image, a method may be employed in which an outline of a candidate area and an outline of a modification area are superimposed upon a specification target image.

The input unit 104 operates the operation device to detect inputs from the user with respect to pixels included in a modification area displayed by the output unit 103 on the display and output user operation information indicated by the detected inputs to the lesion area specification unit 105.

The lesion area specification unit 105 determines (specifies) a lesion area on the basis of a probability image obtained from the probability image calculation unit 102, a candidate area and a modification area obtained from the output unit 103, and user operation information obtained from the input unit 104. A specific method for determining a lesion area will be described later.

Next, the operation of the information terminal 100 configured as above will be described.

Operation

Figure 2:
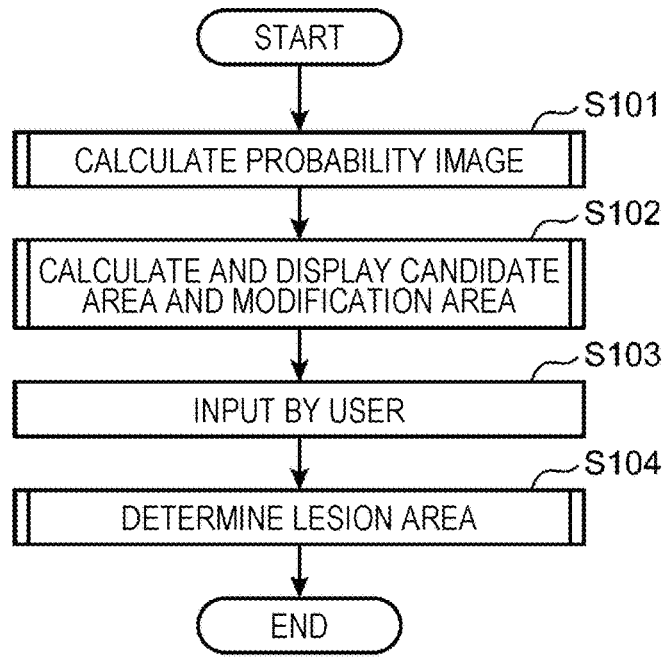
FIG. 2 is a flowchart illustrating an outline of a process performed by the information terminal according to the first embodiment of the present disclosure.

FIG. 2 is a flowchart illustrating an outline of a process performed by the information terminal 100 according to the first embodiment of the present disclosure. First, the probability image calculation unit 102 obtains a specification target image from the case retrieval system 101 and obtains a probability image by calculating a probability value indicating a probability that each pixel of the obtained specification target image is included in a lesion area (S101).

Figure 3:
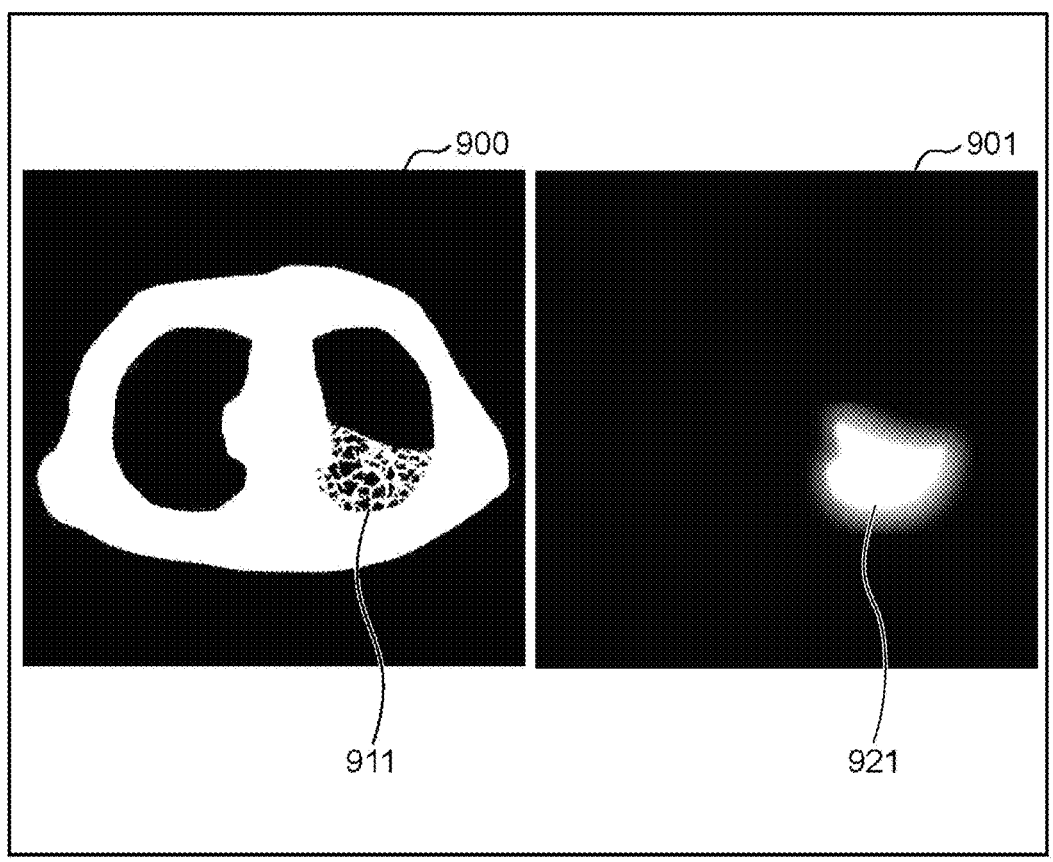
FIG. 3 is a diagram illustrating an example of a lung CT image and an example of a probability image corresponding to the lung CT image.

FIG. 3 is a diagram illustrating an example of a lung CT image 900 and an example of a probability image 901 corresponding to the lung CT image 900. The lung CT image 900 includes a lesion area 911 indicating a lesion of a honeycomb lung. The probability image 901 is obtained by employing, for the lung CT image 900, an identification device that identifies a lesion area of a honeycomb lung. The identification device is obtained, for example, through machine learning. In the probability image 901, a white area 921 indicates an area estimated to be a lesion area, and a black area indicates an area estimated not to be a lesion area.

In the probability image 901, an area 921 is displayed at a position corresponding to the lesion area 911. This means that the lesion area 911 has been correctly extracted from the lung CT image 900.

Figure 4:
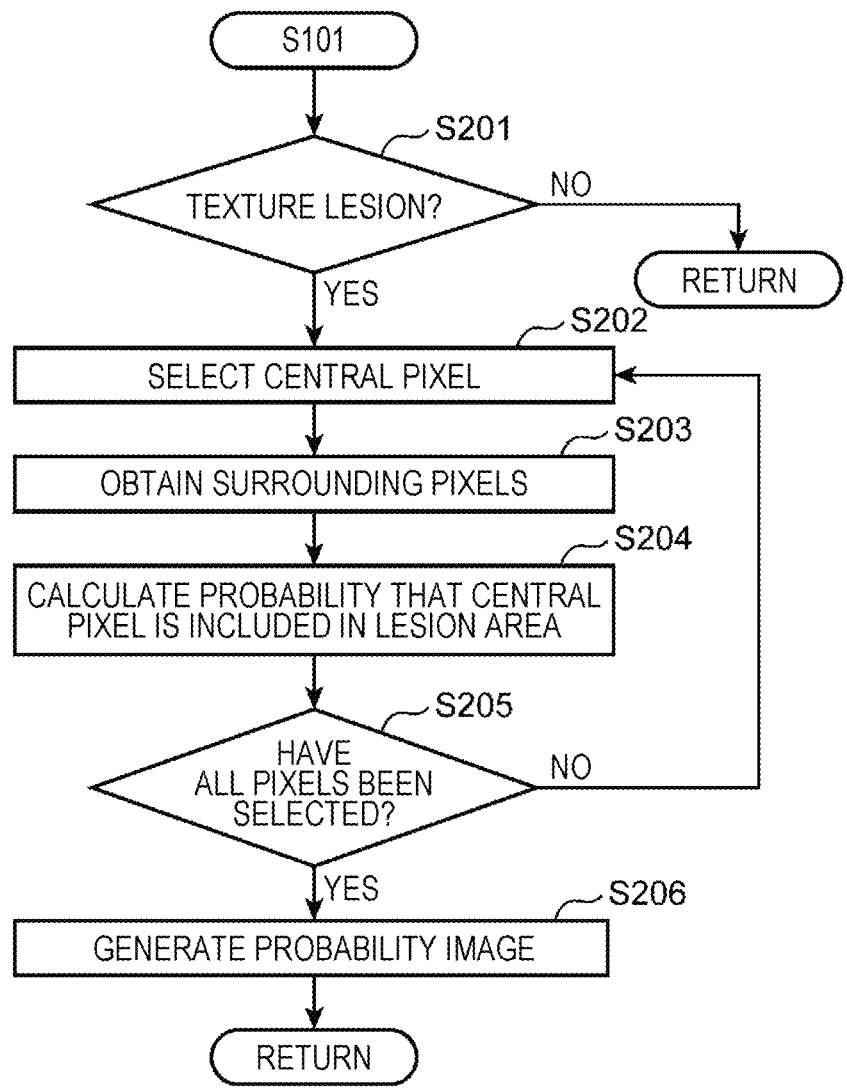
FIG. 4 is a flowchart illustrating details of step S101 illustrated in FIG. 2.

FIG. 4 is a flowchart illustrating details of step S101 illustrated in FIG. 2. A method for calculating a probability image will be described hereinafter with reference to FIG. 4.

First, the probability image calculation unit 102 determines whether a lesion included in a specification target image obtained from the case retrieval system 101 is a texture lesion (step S201). The probability image calculation unit 102 may determine whether the lesion included in the specification target image is a texture lesion, for example, using the method described in "Development of Similar Case Retrieval Technology for Supporting Medical Image Diagnosis and Education of Various Lung Diseases".

In the above example of the related art, a system that retrieves similar medical images for twelve types of lesion has been proposed. The retrieved medical images are given a label indicating the corresponding type of lesion. In this example of the related art, a lesion indicated by a label given to a most similar medical image obtained after medical images similar to an arbitrary medical image are retrieved is determined as a lesion included in the arbitrary medical image. As a result, a type of lesion included in the arbitrary medical image can be determined as one of the twelve types of lesion.

Among the twelve types of lesion used in the above example of the related art, ground glass×nodule, ground glass×uniform, ground glass×multiple medium shadows, multiple granular shadows, and a honeycomb lung are regarded as texture lesions, and the other types of lesion are regarded not as texture lesions. If a label given to a medical image most similar to a specification target image indicates a texture lesion, the probability image calculation unit 102 can determine that the specification target image includes a texture lesion.

Alternatively, the probability image calculation unit 102 may cause the case retrieval system 101 to determine whether a specification target image includes a texture lesion. In this case, the database stored in the case retrieval system 101 includes the medical images to which labels are given. The probability image calculation unit 102 transmits the specification target image to the case retrieval system 101 and receives a medical image most similar to the specification target image from the case retrieval system 101. If a label given to the received medical image indicates a texture lesion, the probability image calculation unit 102 may determine that the specification target image includes a texture lesion.

The case retrieval system 101 may calculate cosine distances between an image feature vector, which represents image feature values extracted from a specification target image as a vector, and image feature vectors of the medical images stored in the database, for example, and determine a medical image having a smallest cosine distance as a medical image most similar to the specification target image.

A scale-invariant feature transform (SIFT) may be used to calculate image feature values. In the SIFT, calculation points of a plurality of feature values are determined in a differential image obtained by smoothing an original image using a plurality of scales, and feature values of 128-bit vectors are obtained on the basis of changes in the luminance of surrounding pixels of the calculation points in a gradient direction of luminance. Feature values independent of rotation, enlargement, or reduction can be obtained as a result of the SIFT. Alternatively, superpixels may be used. Superpixels are used to divide an image into a plurality of areas whose colors or luminances are similar to one another. An average of the colors or the luminances of the obtained areas is used as a feature value.

When the number of feature values calculated is different between images, a feature value of a fixed length may be obtained using a bag of keypoints (BoK). When a BoK is used, a plurality of feature values are converted into a certain number of clusters, and the number of feature values belonging to each duster is handled as a histogram and converted into a feature value of a fixed length, instead.

These are just examples, and other types of image feature value may be employed.

When the information terminal 100 stores a database including medical images to which labels of the twelve types of lesion are given, the probability image calculation unit 102 may retrieve a medical image most similar to a specification target image from the database and determine whether the specification target image includes a texture lesion on the basis of a lesion indicated by a label given to the medical image.

Although labels indicate twelve types of lesion in the above description, labels may indicate thirteen or more types of lesion, instead. In addition, although ground glass×nodule, ground glass×uniform, ground glass×multiple medium shadows, multiple granular shadows, and a honeycomb lung are regarded as texture lesions indicated by labels in the above description, this is just an example. Other types of texture lesion may be used, instead.

Next, the probability image calculation unit 102 selects a pixel in the specification target image obtained from the case retrieval system 101 as a central pixel (step S202). In FIG. 4, the probability image calculation unit 102 repeats steps S202 to S205. By repeatedly performing step S202, the probability image calculation unit 102 may sequentially select a central pixel by performing a raster scan on pixels of the specification target image from an upper-left corner to a lower-right corner.

Next, the probability image calculation unit 102 obtains surrounding pixels of the selected pixel (step S203). The surrounding pixels are, for example, pixels within a square area whose center is the selected pixel and whose side is 31 pixels in length. If the square area does not fit into the specification target image, the probability image calculation unit 102 may set an intermediate value of all possible pixel values as pixel values in a part outside the specification target image. If the specification target image is an 8-bit image, the intermediate value is 255/2=127.5.

Figure 5:
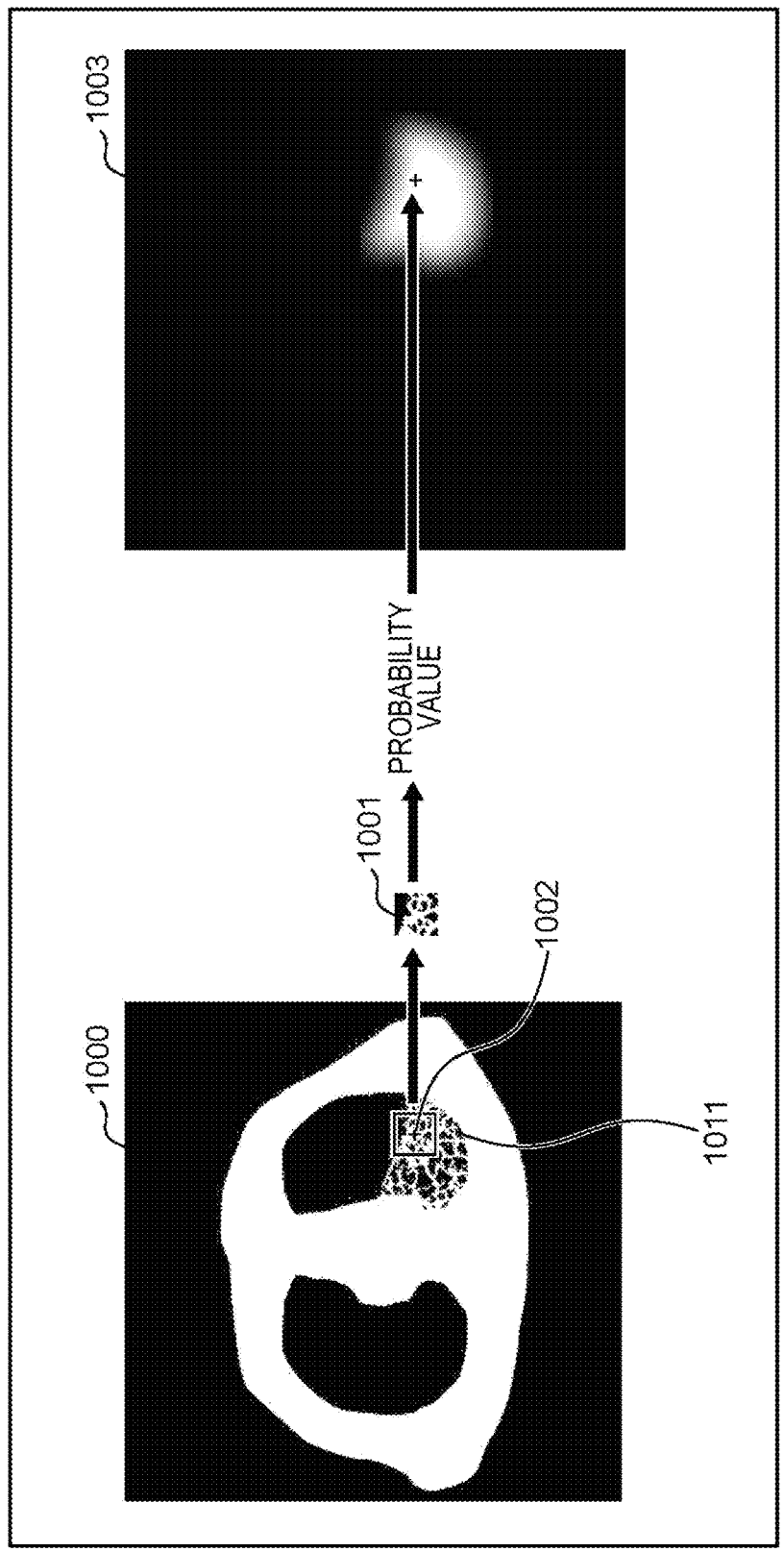
FIG. 5 is a diagram illustrating an example of a specification target image and a probability image generated from the specification target image.

FIG. 5 is a diagram illustrating an example of a specification target image 1000 and a probability image 1003 generated from the specification target image 1000. The specification target image 1000 includes a lesion area 1011 of a honeycomb lung. In the example illustrated in FIG. 5, a pixel in the lesion area 1011 is selected as a central pixel 1002.

Next, the probability image calculation unit 102 inputs, to an identification device, pixel values of pixels of a local area image, which includes the central pixel selected in step S202 and the surrounding pixels, in order to calculate a probability value indicating a probability that the central pixel is included in a lesion area (step S204). The probability image calculation unit 102 may calculate the probability value, for example, using the method for identifying a lesion described in "Analysis for Deep Convolutional Neural Network Feature with Diffuse Lung Disease Classification".

In the above example of the related art, a method for configuring an identification device that determines which of one type of image including a normal area and six types of image including a lesion area an image to be identified belongs to has been disclosed. More specifically, in this example of the related art, a method for calculating a probability value indicating a probability that each of pixels of an image to be identified belongs to each of the seven types of image has been disclosed. The probability image calculation unit 102, therefore, may input, to the identification device described in the above example of the related art, the pixel values of the pixels of the local area image, calculate a probability value indicating a probability that the central pixel is included in each of the six types of image including a lesion area, and determine the sum of the six probability values as the probability value of the central pixel. Alternatively, the probability image calculation unit 102 may calculate a probability value indicating a probability that the central pixel is included in the one type of image including a normal area and determine a value obtained by subtracting 1 from the probability value as the probability value of the central pixel. As a result, each of the pixels of the probability image obtains a probability value equal to or larger than 0 but equal to or smaller than 1. The identification device may be obtained through machine learning, and medical images in which lesion areas have been specified stored in the case retrieval system 101, for example, may be used as learning data used in the machine learning.

In the example illustrated in FIG. 5, an area of a certain size whose center is the central pixel 1002 is set as the local area image 1001. The local area image 1001 is input to the identification device, and the probability value of the central pixel 1002 is calculated.

Next, the probability image calculation unit 102 determines whether all the pixels of the specification target image have been selected in step S201 as a central pixel (step S205). If all the pixels have been selected as a central pixel (YES in step S205), the process proceeds to step S206. If not all the pixels have been selected as a central pixel (NO in step S205), the process returns to step S202. As a result, the pixels of the specification target image are sequentially selected as a central pixel, and probability values of the central pixels are calculated.

Next, the probability image calculation unit 102 generates a probability image whose pixels have pixel values corresponding to the probability values calculated for the pixels of the specification target image (step S206). As a result, the probability image 1003 according to the probability values illustrated in FIG. 5 is generated.

By performing steps S201 to S206, a probability image whose pixels have pixel values corresponding to probability values indicating probabilities that pixels of a specification target image are included in a lesion area is calculated. After step S206, the process proceeds to step S102 illustrated in FIG. 2.

In step S102 illustrated in FIG. 2, the output unit 103 determines, in the probability image obtained from the probability image calculation unit 102, an area whose pixels have probability values equal to or larger than the first threshold as a candidate area and an area whose pixels have probability values within a probability range including the first threshold as a modification area. The output unit 103 then transmits the candidate area and the modification area to the lesion area specification unit 105 and displays, on the display, a medical image obtained by superimposing the candidate area and the modification area upon the specification target image obtained from the probability image calculation unit 102.

Figure 6:
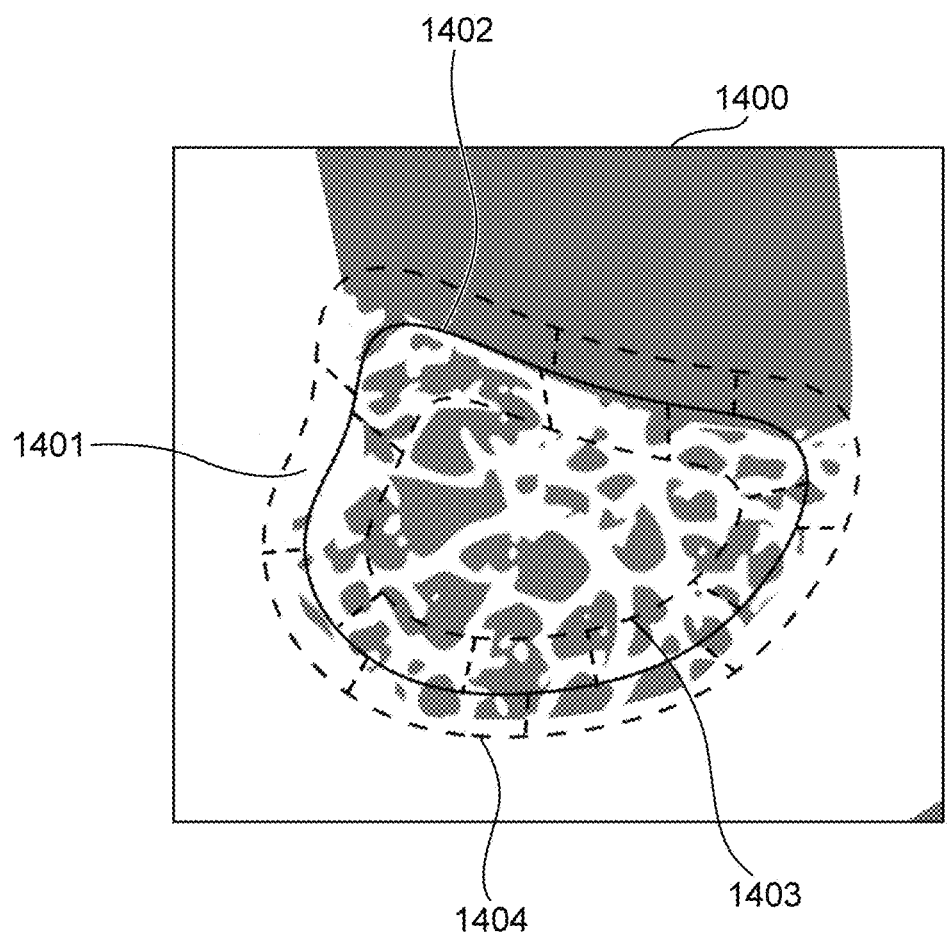
FIG. 6 is a diagram illustrating an example of a medical image obtained by superimposing a candidate area and a modification area upon a specification target image.

FIG. 6 is a diagram illustrating an example of a medical image 1400 obtained by superimposing a candidate area and a modification area upon a specification target image. In the medical image 1400 (an example of a second medical image) illustrated in FIG. 6, a modification area 1401 and a candidate area 1402 are superimposed upon the medical image 1400. The candidate area 1402 is an area defined by a solid line. The modification area 1401 is an area defined by broken lines 1403 and 1404. That is, an inner circumference of the modification area 1401 is inside the candidate area 1402, and an outer circumference of the modification area 1401 is outside the candidate area 1402.

Figure 7:
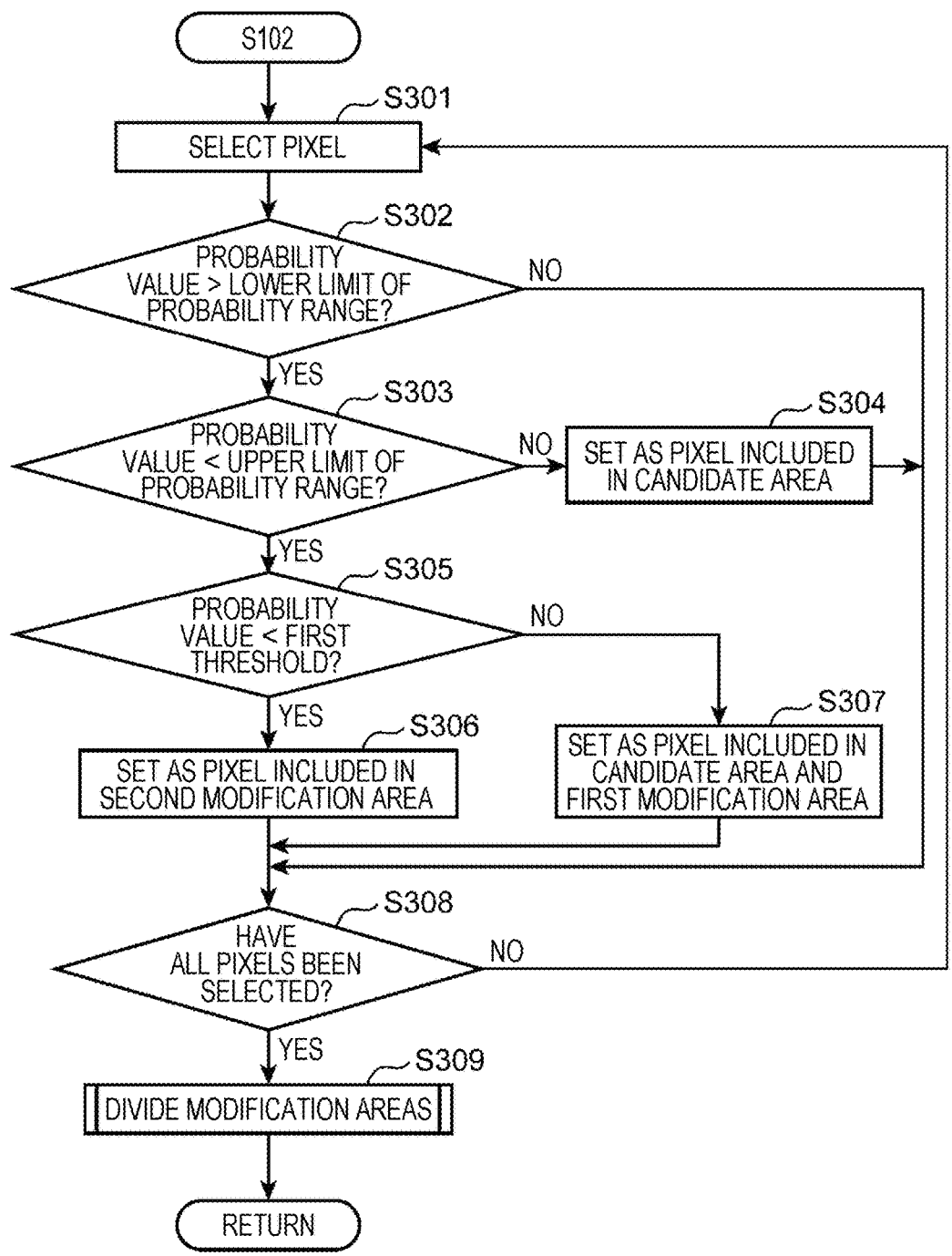
FIG. 7 is a flowchart illustrating details of step S102 illustrated in FIG. 2.

FIG. 7 is a flowchart illustrating details of step S102 illustrated in FIG. 2. A method for calculating a candidate area and a modification area will be described hereinafter with reference to FIG. 7.

First, the output unit 103 selects a pixel in a probability image obtained from the probability image calculation unit 102 (step S301). For example, the output unit 103 may sequentially select a pixel by performing a raster scan on pixels of the probability image from an upper-left corner to a lower-right corner.

Next, the output unit 103 determines whether a probability value of the pixel selected in step S301 is larger than a lower limit of a probability range (step S302). If the probability value of the selected pixel is larger than the lower limit of the probability range (YES in step S302), the process proceeds to step S303. If the probability value of the selected pixel is not larger than the lower limit of the probability range (NO in step S302), the process proceeds to step S308. As the lower limit of the probability range, an empirically obtained smallest possible probability value of a pixel in a lesion area, namely 0.3, for example, may be used. This is just an example, and any other value smaller than the first threshold (e.g., 0.1, 0.2, 0.4, etc.) may be used, instead.

Next, the output unit 103 determines whether the probability value of the pixel selected in step S301 is smaller than an upper limit of the probability range (step S303). If the probability value of the selected pixel is smaller than the upper limit of the probability range (YES in step S303), the process proceeds to step S305. If the probability value of the selected pixel is not smaller than the upper limit of the probability range (NO in step S305), on the other hand, the output unit 103 sets the pixel selected in step S301 as a pixel included in a candidate area (step S304), and the process proceeds to step S308.

That is, a pixel whose probability value is equal to or larger than the upper limit of the probability range is determined as a pixel belonging to the candidate area.

The upper limit of the probability range may be a value just below an empirically obtained smallest possible probability value with which it can be affirmed that a corresponding pixel belongs to a candidate area, namely 0.9, for example, may be used. This is just an example, and any other value (e.g., 0.6, 0.7, 0.8, etc.) larger than the first threshold may be used, instead.

Next, the output unit 103 determines whether the probability value of the pixel selected in step S301 is smaller than the first threshold (step S305). If the probability value of the selected pixel is smaller than the first threshold (YES in step S305), the output unit 103 sets the selected pixel as a pixel included in a second modification area (step S306).

That is, a pixel whose probability value is between the lower limit of the probability range and the first threshold is determined as a pixel belonging to the second modification area.

If the probability value of the selected pixel is not smaller than the first threshold (NO in step S305), the output unit 103 sets the selected pixel as a pixel belonging to the candidate area and a first modification area (step S307).

That is, a pixel whose probability value is equal to or larger than the first threshold but smaller than the upper limit of the probability value is determined as a pixel belonging to the candidate area and the first modification area. When the first and second modification areas are not particularly distinguished from each other, they will be generically referred to as "modification areas" in the following description.

As the first threshold, a value just below an empirically obtained smallest possible probability value likely to indicate a lesion area, that is, a value just below an empirically obtained smallest possible probability value with which it is reasonable to determine that a corresponding pixel belongs to the candidate area, namely 0.6, for example, may be used.

Next, the output unit 103 determines whether all pixels of the probability image obtained from the probability image calculation unit 102 in step S102 have been selected (step S308). If all the pixels have been selected (YES in step S308), the process proceeds to step S309. If not all the pixels have been selected (NO in step S308), the process returns to step S301, and a next pixel is selected in the probability image.

Figure 8:
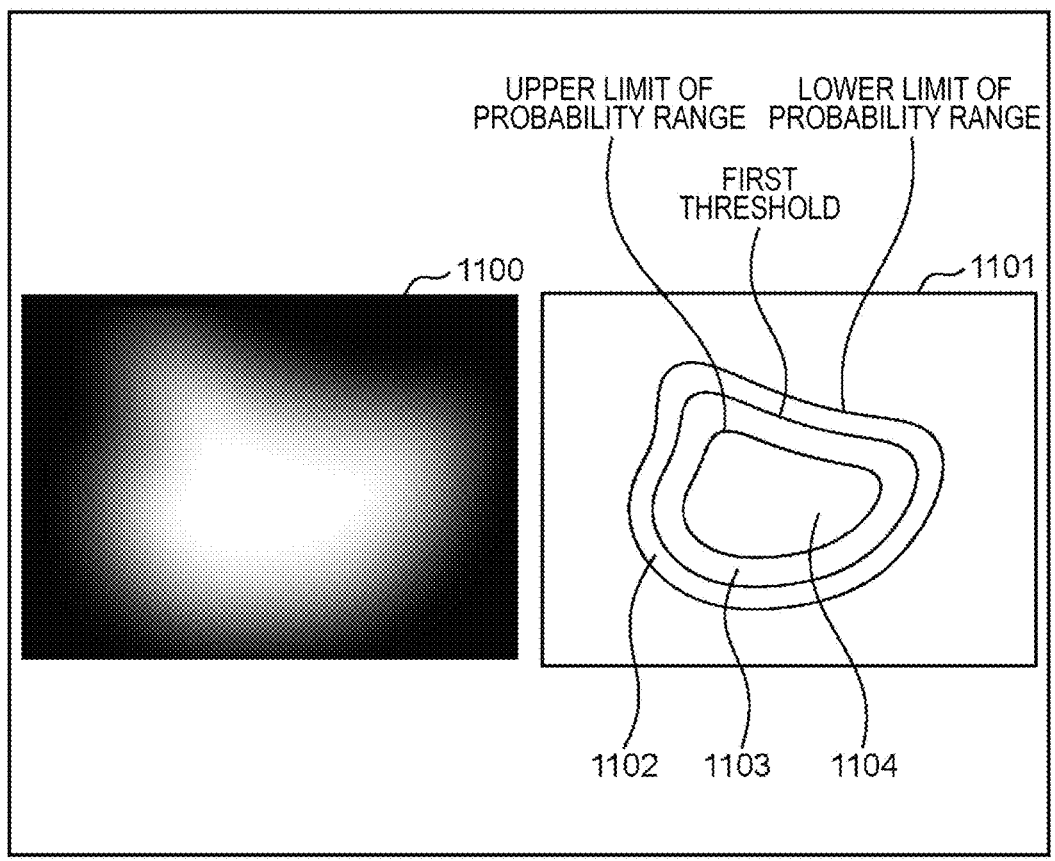
FIG. 8 is a diagram illustrating an example of a probability image, a candidate area calculated from the probability image, a first modification area, and a second modification area.

FIG. 8 is a diagram illustrating an example of a probability image 1100 and a candidate area, a first modification area, and a second modification area calculated from the probability image 1100. The probability image 1100 corresponds to a part of the probability image 1003 (refer to FIG. 5) in which probability values are large. In the probability image 1100, probability values are largest at the center.

An image 1101 includes outlines of the modification areas and the candidate area set in the probability image 1100.

In FIG. 8, an outermost closed curve is an isopleth of the lower limit of the probability range. An innermost closed curve is an isopleth of the upper limit of the probability range. An intermediate closed line is an isopleth of the first threshold.

An area 1102 is defined by the isopleth of the lower limit of the probability range and the isopleth of the first threshold and indicates the second modification area. An area 1103 is defined by the isopleth of the first threshold and the isopleth of the upper limit of the probability range and indicates the candidate area and the first modification area. An area 1104 is defined by the isopleth of the upper limit of the probability range and indicates the candidate area. The candidate area corresponds to the areas 1103 and 1104.

Since probability values are largest at the center of a texture lesion area, the area 1102 (second modification area), the area 1103 (the candidate area and the first modification area), and the area 1104 (the candidate area and not the first modification area or the second modification area) are observed in this order toward the center of the image 1101.

In step S309 illustrated in FIG. 7, the output unit 103 divides the first and second modification areas set in steps S307 and S306, respectively, into sub-areas (step S309).

The sub-areas refer to areas obtained by dividing the first and second modification areas.

Figure 9:
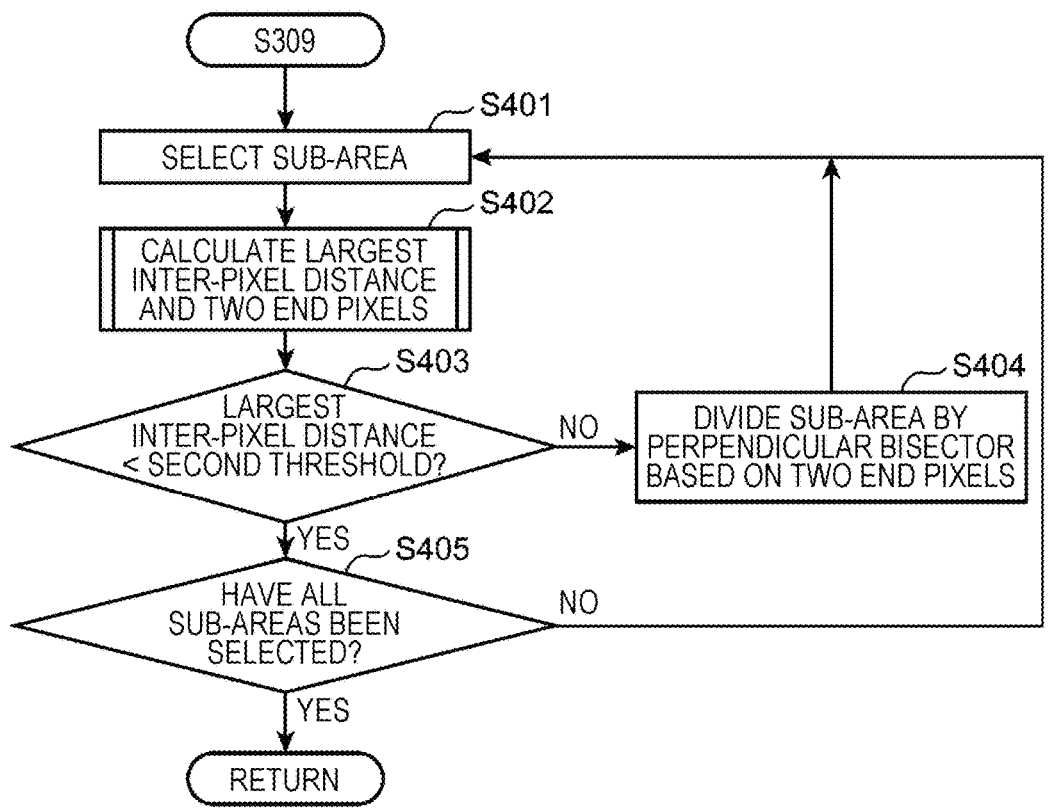
FIG. 9 is a flowchart illustrating details of step S309 illustrated in FIG. 7.

FIG. 9 is a flowchart illustrating details of step S309 illustrated in FIG. 7. A method for calculating sub-areas will be described hereinafter with reference to FIG. 9.

First, the output unit 103 selects a sub-area in the modification areas (step S401). When step S401 is performed for the first time, the first and second modification areas have been divided into sub-areas. The output unit 103 may sequentially select sub-areas in the image from left to right, for example, on the basis of positions of left ends of the sub-areas. This, however, is just an example, and the output unit 103 may sequentially select sub-areas in another order, namely, for example, from top to bottom on the basis of positions of upper ends of the sub-areas, instead.

Next, the output unit 103 calculates a largest inter-pixel distance of the sub-area selected in step S401 and two end pixels used to obtain the largest inter-pixel distance (step S402).

Figure 10:
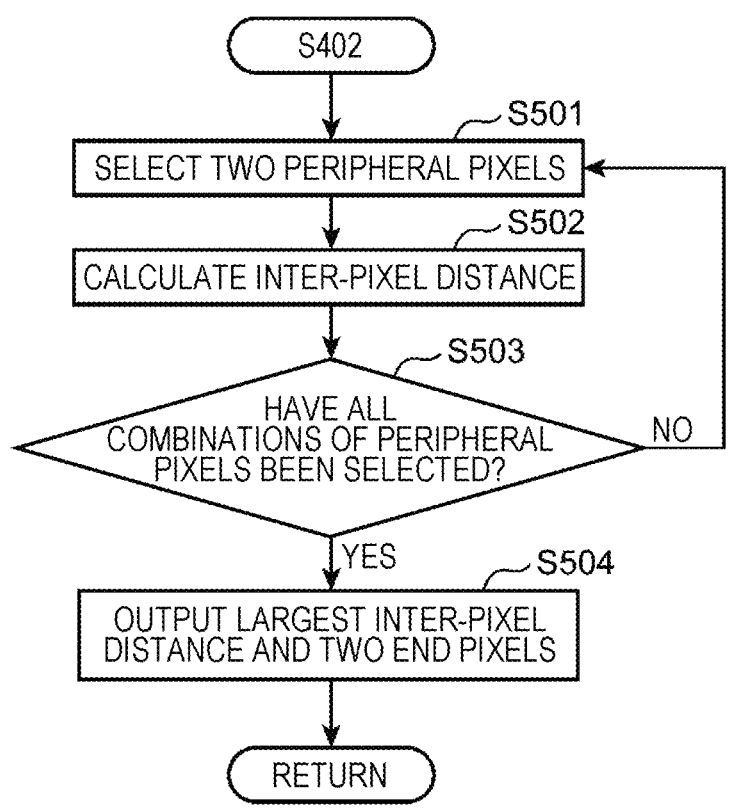
FIG. 10 is a flowchart illustrating details of step S402 illustrated in FIG. 9.

FIG. 10 is a flowchart illustrating details of step S402 illustrated in FIG. 9. A method for calculating a largest inter-pixel distance and two end pixels will be described hereinafter with reference to FIG. 10.

First, the output unit 103 selects two peripheral pixels of the sub-area selected in step S401 (step S501). The output unit 103 may select the two pixels, for example, by fixing one of the two pixels and sequentially trying other peripheral pixels.

Next, the output unit 103 calculates an inter-pixel distance between the two pixels selected in step S501 (step S502). The inter-pixel distance is a distance between two pixels in an image.

Next, the output unit 103 determines whether all pixels have been selected in step S501 (step S503). If all the pixels have been selected (YES in step S503), the process proceeds to step S504. If not all the pixels have been selected (NO in step S503), the process proceeds to step S501.

Next, the output unit 103 determines a largest one of inter-pixel distances calculated in step S503 as a largest inter-pixel distance and two end pixels corresponding to the largest inter-pixel distance and outputs the largest inter-pixel distance and the two end pixels (step S504). After step S504, the process proceeds to step S403 illustrated in FIG. 9.

Figure 11:
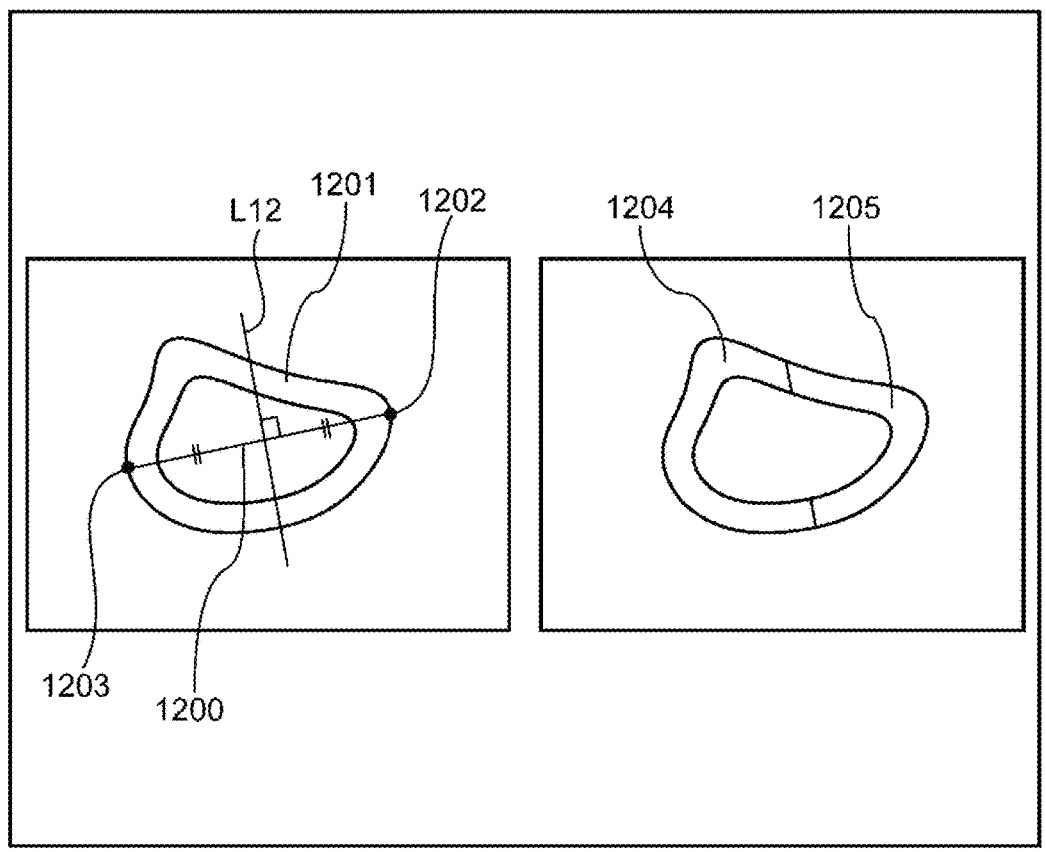
FIG. 11 is a diagram illustrating an example of a process for dividing a sub-area.

FIG. 11 is a diagram illustrating an example of a process for dividing a sub-area 1201. In FIG. 11, a left image indicates the sub-area 1201 before division, and a right image indicates sub-areas 1204 and 1205 obtained as a result of the division. The sub-area 1201 has been selected in step S401. A segment 1200 indicates a largest inter-pixel distance. Points 1202 and 1203 are two end pixels of the segment 1200.

By performing steps S501 to S504, the largest inter-pixel distance (segment 1200) of the sub-area 1201 selected in step S401 and the two end pixels (points 1202 and 1203) corresponding to the largest inter-pixel distance are calculated.

In FIG. 9, the output unit 103 determines in step S403 whether the largest inter-pixel distance calculated in step S402 is smaller than a second threshold (step S403). If the largest inter-pixel distance is smaller than the second threshold (YES in step S403), the process proceeds to step S405. If the largest inter-pixel distance is not smaller than the second threshold (NO in step S403), the process proceeds to step S404.

Next, the output unit 103 sets a perpendicular bisector of a segment connecting the two end pixels corresponding to the largest inter-pixel distance calculated in step S402 and divides the sub-area selected in step S401 by the perpendicular bisector (step S404). The process then returns to step S401. Two areas obtained as a result of the division performed in step S404 are set as new sub-areas and can be selected in step S401.

In FIG. 11, a perpendicular bisector L12 is set for the segment 1200, and the sub-area 1201 is divided into the two sub-areas 1204 and 1205 by the perpendicular bisector L12.

In FIG. 9, the output unit 103 determines in step S405 whether all the sub-areas have been selected in step S401. If all the sub-areas have been selected (YES in step S405), step S309 illustrated in FIG. 7 ends, and the process proceeds to step S103 illustrated in FIG. 2. If not all the sub-areas have been selected (NO in step S405), the process returns to step S401.

By performing steps S401 to S405, the first and second modification areas set in steps S307 and S306, respectively, are divided into sub-areas whose largest inter-pixel distances are smaller than the second threshold.

In FIG. 2, the input unit 104 detects, in step S103, an input by the user on a pixel in the modification areas of the medical image obtained by superimposing the candidate area and the modification areas upon the specification target image through the operation device. The input unit 104 then transmits user operation information indicated by the detected input to the lesion area specification unit 105. The user operation information includes, for example, coordinates of the pixel at a position at which the user has performed a click operation.

Next, the lesion area specification unit 105 determines a lesion area on the basis of the probability image obtained from the probability image calculation unit 102, the candidate area obtained from the output unit 103, and the user operation information obtained from the input unit 104 (step S104).

Figure 12:
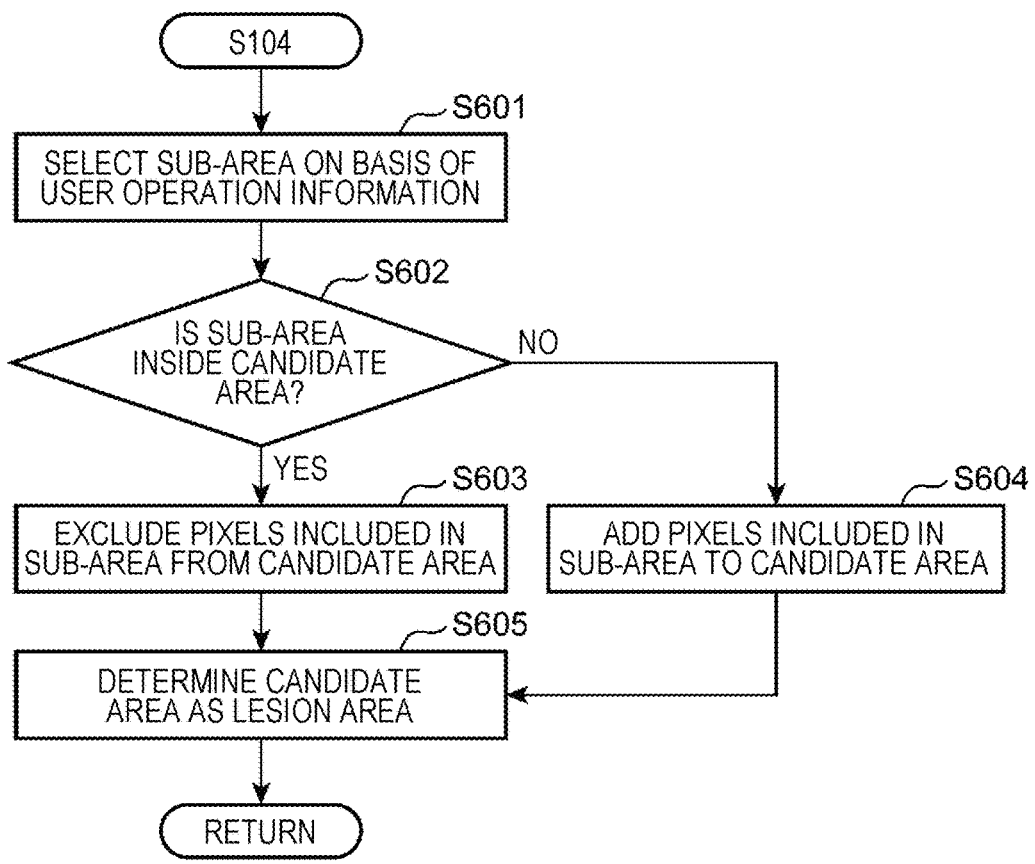
FIG. 12 is a flowchart illustrating details of step S104 illustrated in FIG. 2.

FIG. 12 is a flowchart illustrating details of step S104 illustrated in FIG. 2. A method for determining a lesion area will be described hereinafter with reference to FIG. 12.

First, the lesion area specification unit 105 selects a sub-area on the basis of the user operation information obtained in step S103 (step S601). If a plurality of sub-areas have been specified in step S103, the plurality of sub-areas are selected in step S601, and step S602 and later steps are performed for each of the plurality of sub-areas.

Figure 13:
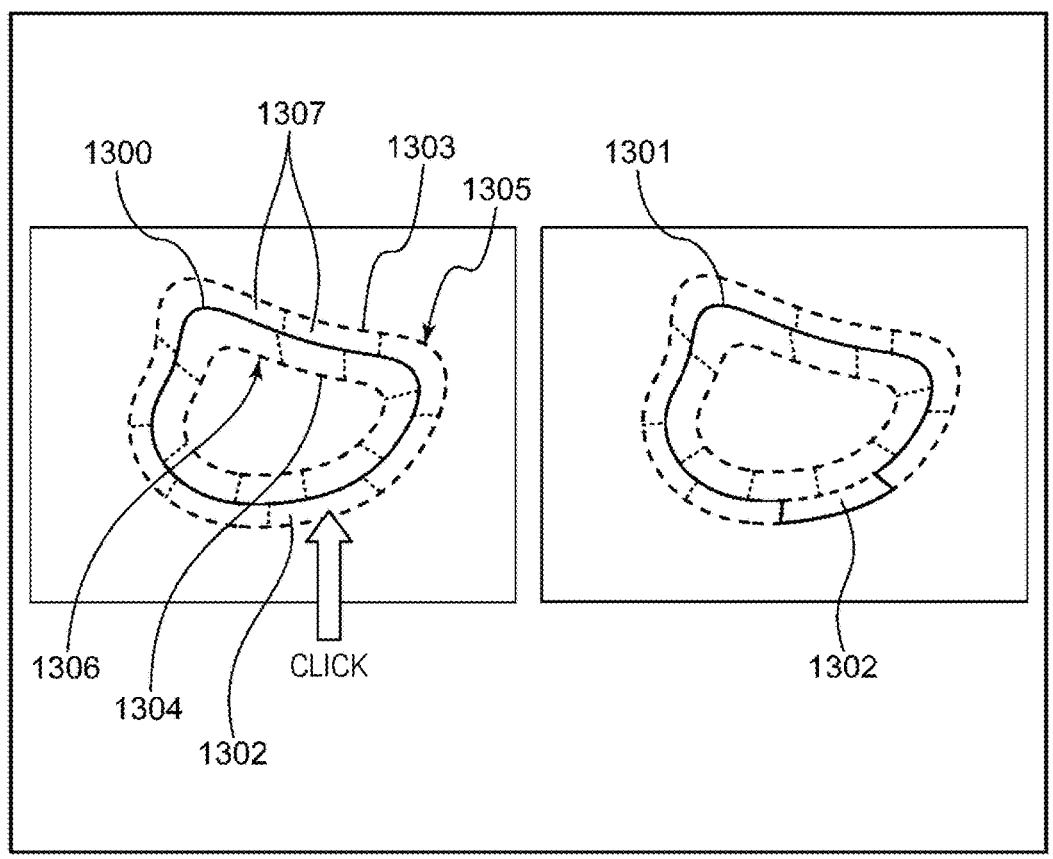
FIG. 13 is a diagram illustrating an operation for selecting a sub-area performed by a user.

FIG. 13 is a diagram illustrating an operation for selecting a sub-area performed by the user. In FIG. 13, a left image indicates a state before a sub-area is selected, and a right image indicates a state after a sub-area is selected. In FIG. 13, a boundary line 1300 is an isopleth of the first threshold. That is, an area inside the boundary line 1300 is a candidate area. A broken line 1303 is an outer circumference of a first modification area, and a broken line 1304 is an inner circumference of a second modification area. That is, an area 1305 defined by the broken line 1303 and the boundary line 1300 is the second modification area, and an area 1306 defined by the boundary line 1300 and the broken line 1304 is the first modification area. An area 1306 is also the candidate area.

The area 1305, which is the second modification area, and the area 1306, which is the first modification area, have been divided into sub-areas 1307.

In the left image of FIG. 13, the user clicks a mouse with a mouse pointer positioned in a sub-area 1302. As a result, the sub-area 1302 among the sub-areas 1307 is selected.

In step S602 illustrated in FIG. 12, the lesion area specification unit 105 determines whether the sub-area selected in step S601 is inside the candidate area calculated in step S102. Since the sub-area 1302 is outside the boundary line 1300 in the example illustrated in FIG. 13, the lesion area specification unit 105 determines that the sub-area 1302 is outside the candidate area.

Next, if determining that the sub-area selected in step S601 is inside the candidate area (YES in step S602), the lesion area specification unit 105 excludes pixels of the sub-area from the candidate area (step S603) to modify the candidate area. If determining that the sub-area selected in step S601 is not inside the candidate area (NO in step S602), on the other hand, the lesion area specification unit 105 adds the pixels of the sub-area to the candidate area (step S604) to modify the candidate area. The modified candidate area will be referred to as a "modified candidate area" hereinafter.

As indicated in the right image of FIG. 13, pixels of the sub-area 1302 selected in the left image are added to the candidate area, and a new boundary line 1301 of the candidate area is set such that the candidate area includes the sub-area 1302. An area inside the boundary line 1301 is a modified candidate area. If the sub-area 1302 is inside the candidate area, a new boundary line 1301 of the candidate area is set such that the candidate area excludes the sub-area 1302.

Next, the lesion area specification unit 105 determines the modified candidate area calculated in steps S603 and S604 as a lesion area (step S605). When step S605 ends, step S104 illustrated in FIG. 2 also ends, and the flowchart of FIG. 2 ends. By performing steps S601 to S605, the candidate area is modified in accordance with a user operation for selecting a sub-area, and a lesion area is finally determined.

If the candidate area need not be modified, the process ends while skipping steps S601 to S605. In addition, if the candidate area need not be modified, the user may input an operation indicating that the candidate area need not be modified in order to skip steps S601 to S605. In addition, steps S601 to S605 may be repeated until the user inputs an instruction to stop modifying the candidate area, and the user may select a plurality of sub-areas.

Next, a reason why a specification target image including a texture lesion is to be processed will be described.

As described above, a probability value indicating a probability that each of pixels of a specification target image is included in a lesion area is calculated by setting, as a local area image, an area of a certain size whose central pixel is the pixel and inputting the local area image to an identification device. If the specification target image includes a texture lesion area, the local area image exhibits a characteristic pattern indicating a texture lesion regardless of which pixel in the lesion area has been used as the central pixel of the local area image. If the specification target image includes a non-texture lesion area, on the other hand, a characteristic pattern appears in the periphery of a lesion area. If a local area image is set for a non-texture lesion and identification of a lesion is performed, therefore, the lesion can be appropriately identified insofar as the local area image is set in the periphery of the lesion area. If the local area image is not set in the periphery of the lesion area, however, a characteristic pattern might not appear, and the lesion might not be appropriately identified. When a local area image is set for a specification target image including a non-texture lesion area and identification of a lesion is performed, therefore, a candidate area including pixels whose probability values are equal to or larger than the first threshold might appear at a position far from an actual lesion area. In the case of a specification target image including a non-texture lesion area, therefore, it is not appropriate to determine a lesion area on the basis of a candidate area calculated using a probability image, and a lesion area is not efficiently determined.

In the present embodiment, therefore, a specification target image including a texture lesion area is to be processed. In so doing, a candidate area far from an actual lesion area is not calculated, and work efficiency improves.

The information terminal 100 according to the present embodiment thus processes a specification target image including a texture lesion area, calculates a candidate area and modification areas from the specification target image, and presents the candidate area and the modification areas to the user. As a result, the candidate area and the modification areas that substantially match an actual lesion area can be presented to the user. In addition, the information terminal 100 divides the modification areas into a plurality of sub-areas and presents the divided modification areas to the user. As a result, the user can determine a final lesion area by clicking on a sub-area to be added to or excluded from a candidate area. The user can thus easily and promptly determine a lesion area.

Second Embodiment

Next, a second embodiment of the present disclosure will be described. In the second embodiment, the user drags an isopleth of the first threshold to modify a candidate area. In the second embodiment, the same components as those according to the first embodiment are given the same reference numerals, and description thereof is omitted. The configuration of an information terminal 100 according to the second embodiment is the same as that illustrated in FIG. 2.

Operation

The operation of the information terminal 100 according to the second embodiment will be described with reference to FIG. 2. The calculation of a probability image in step S101 is the same as in the first embodiment, and description thereof is omitted.

In step S102, the output unit 103 calculates, in the probability image obtained from the probability image calculation unit 102, an area including pixels whose probability values are equal to or larger than the first threshold as a candidate area and an area including pixels whose probability values are within the probability range including the first threshold as a modification area. The output unit 103 then transmits the candidate area and the modification area to the lesion area specification unit 105 and displays, on the display, a medical image obtained by superimposing the candidate area and the modification area upon the specification target image obtained from the probability image calculation unit 102.

Figure 14:
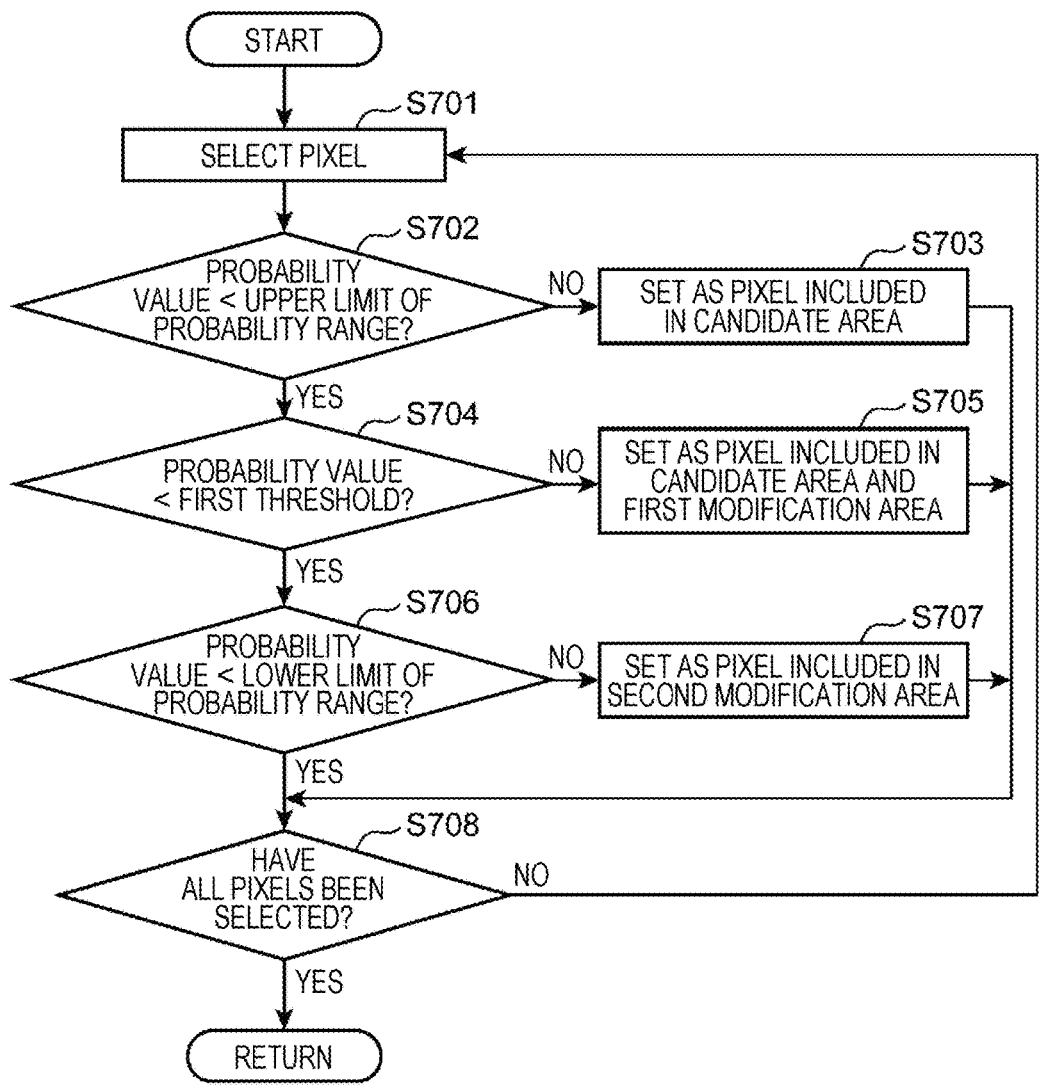
FIG. 14 is a flowchart illustrating details of step S102 illustrated in FIG. 2 according to a second embodiment of the present disclosure.

FIG. 14 is a flowchart illustrating details of step S102 illustrated in FIG. 2 according to the second embodiment of the present disclosure. A method for calculating a candidate area and a modification area will be described hereinafter with reference to FIG. 14.

First, the output unit 103 selects a pixel in the probability image obtained from the probability image calculation unit 102 (step S701). Details of step S701 are the same as those of step S301 illustrated in FIG. 7.

Next, the output unit 103 determines whether a probability value of the pixel selected in step S701 is smaller than the upper limit of the probability range (step S702). If the probability value of the selected pixel is smaller than the upper limit of the probability range (YES in step S702), the process proceeds to step S704. If the probability value of the selected pixel is not smaller than the upper limit of the probability range (NO in step S702), the output unit 103 sets the selected pixel as a pixel included in the candidate area (step S703), and the process proceeds to step S708. That is, a pixel whose probability value is equal to or larger than the upper limit of the probability range is determined as a pixel belonging to the candidate area. The upper limit of the probability range may be 0.9, for example, as in the first embodiment.

Next, the output unit 103 determines whether the probability value of the pixel selected in step S701 is smaller than the first threshold (step S704). If the probability value of the selected pixel is smaller than the first threshold (YES in step S704), the process proceeds to step S706. If the probability value of the selected pixel is not smaller than the first threshold (NO in step S704), the output unit 103 sets the selected pixel as a pixel included in the candidate area and the first modification area (step S705), and the process proceeds to step S708. That is, a pixel whose probability value is equal to or larger than the first threshold but smaller than the upper limit of the probability range is determined as a pixel belonging to the candidate area and the first modification area. The first threshold may be 0.6, for example, as in the first embodiment.

Next, the output unit 103 determines whether the probability value of the pixel selected in step S701 is smaller than the lower limit of the probability range (step S706). If the probability value of the pixel is smaller than the lower limit of the probability range (YES in step S706), the process proceeds to step S708. If the probability value of the selected pixel is not smaller than the lower limit of the probability range (NO in step S706), the output unit 103 sets the selected pixel as a pixel belonging to the second modification area (step S707). That is, a pixel whose probability value is equal to or larger than the lower limit of the probability value but smaller than the first threshold is determined as a pixel belonging to the second modification area. The lower limit of the probability range may be 0.3, for example, as in the first embodiment.

Next, the output unit 103 determines whether all pixels of the probability image obtained from the probability image calculation unit 102 in step S701 have been selected (step S708). If all the pixels have been selected, the process ends. If not all the pixels have been selected (NO in step S708), the process returns to step S701, and a next pixel is selected in the probability image.

By performing steps S701 to S708, the candidate area and the first and second modification areas can be calculated in step S102.

In FIG. 2, the input unit 104 detects, in step S103, an input by the user on a pixel in the modification areas of the medical image obtained by superimposing the candidate area and the modification areas upon the specification target image through the operation device. The input unit 104 then transmits user operation information indicated by the detected input to the lesion area specification unit 105. The user operation information includes, for example, coordinates of the pixel at a start point of a drag operation performed by the user and the amount of movement in the drag operation. The amount of movement in the drag operation may be, for example, the amount of movement in a normal line direction of an isopleth passing through the start point of the drag operation. For example, the input unit 104 may calculate the amount of movement by projecting a segment connecting the start point of the drag operation and an end point of the drag operation in the normal line direction. If a drag operation in a direction in which the candidate area is enlarged is input, for example, a negative amount of movement is used, and if a drag operation in a direction in which the candidate area is reduced is input, a positive amount of movement is used.

Next, the lesion area specification unit 105 determines a lesion area on the basis of the probability image obtained from the probability image calculation unit 102, the candidate area and the modification areas obtained from the output unit 103, and the user operation information obtained from the input unit 104 (step S104).

Figure 15:
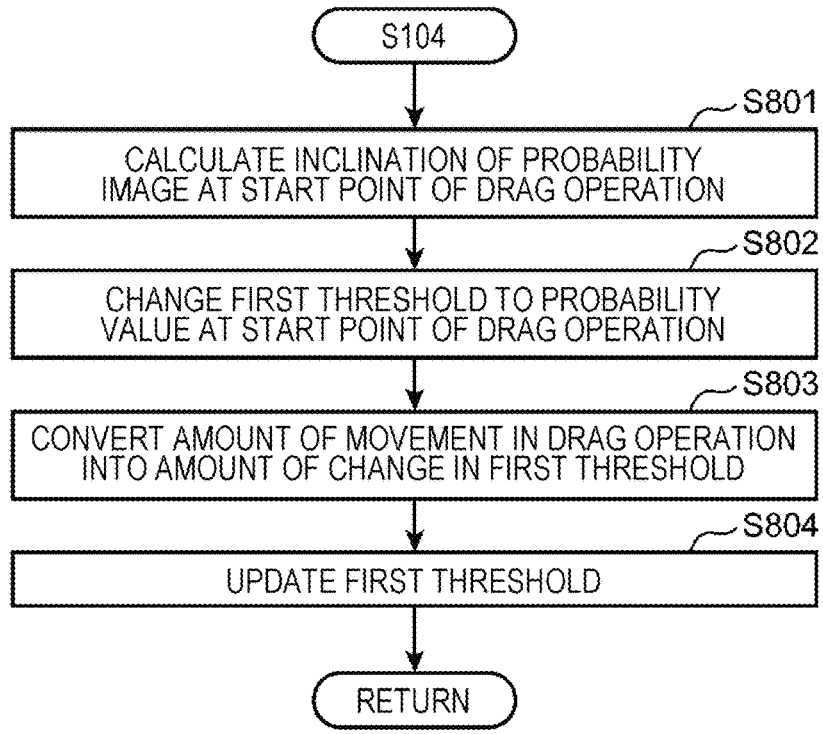
FIG. 15 is a flowchart illustrating details of step S104 illustrated in FIG. 2 according to the second embodiment of the present disclosure.

FIG. 15 is a flowchart illustrating details of step S104 illustrated in FIG. 2 according to the second embodiment of the present disclosure. A method for specifying a lesion area will be described hereinafter with reference to FIG. 15.

First, the lesion area specification unit 105 calculates an inclination of the probability image at the start point of the drag operation on the basis of the user operation information obtained in step S103 (step S801).

Figure 16:
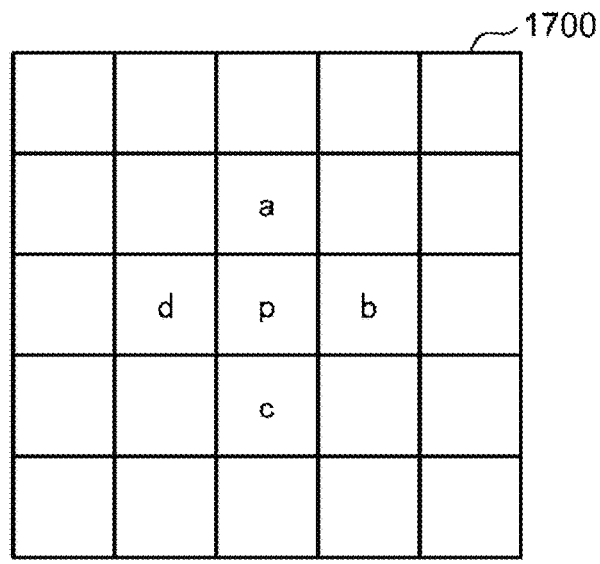
FIG. 16 is a schematic diagram illustrating a probability value of a pixel at a start point of a drag operation and probability values of surrounding pixels in a probability image.

FIG. 16 is a schematic diagram illustrating a probability value p of a pixel at a start point of a drag operation and probability values of surrounding pixels of the probability value p in a probability image 1700. In the example of the probability image 1700, an area including 25 pixels including the pixel at the start point of the drag operation is indicated. A method for calculating an inclination of a probability image will be described hereinafter with reference to FIG. 16.

In the calculation of an inclination, probability values a to d of pixels adjacent to the pixel at the start point of the drag operation in upward, rightward, downward, and leftward directions, respectively, are used. The inclination of the pixel at the start point of the drag operation is calculated on the basis of the following expression (1) using these probability values a to d.

$$\{(\{b-d\}/2)^2+(\{c-a\}/2)^2\}^{0.5} \quad (1)$$

Although the inclination is calculated here using the probability values of the four pixels adjacent to the pixel at the start point of the drag operation in the upward, rightward, downward, and leftward directions, respectively, the calculation method is not limited to this. For example, an inclination may be calculated using probability values of two pixels adjacent to a pixel at a start point of a drag operation in upward and rightward directions, respectively, instead.

An expression used in this case is, for example, the following expression (2).

$$\{(\{b-a\}/2)^2\}^{0.5} \quad (2)$$

This, however, is just an example, and an inclination may be calculated using probability values of two pixels adjacent to a pixel at a start point of a drag operation in rightward and downward directions, respectively, probability values of two pixels adjacent to a pixel at a start point of a drag operation in downward and leftward directions, respectively, or probability values of two pixels adjacent to a pixel at a start point of a drag operation in leftward and upward directions, respectively.

Alternatively, an inclination may be calculated using probability values of pixels distant from a pixel at a start point of a drag operation by two or more pixels. Alternatively, an inclination may be calculated using pixels diagonally adjacent to a pixel at a start point of a drag operation.

In FIG. 15, the lesion area specification unit 105 changes, in step S802, the first threshold to the probability value p of the pixel at the start point of the drag operation.

Figure 17:
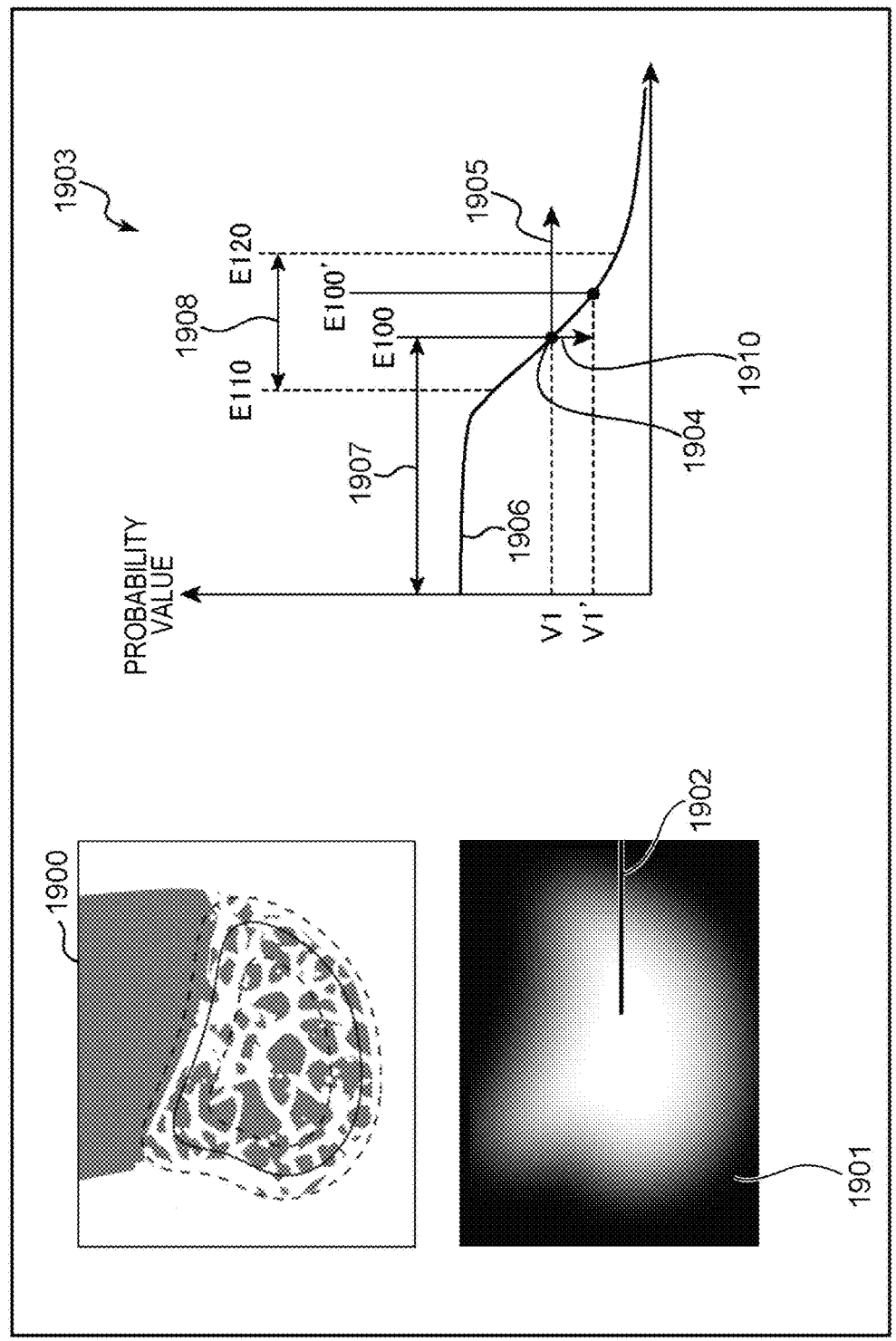
FIG. 17 is a diagram illustrating a method for calculating the amount of change in a first threshold.

Next, the lesion area specification unit 105 calculates the amount of change in the first threshold on the basis of the amount of movement in the drag operation and the inclination of the probability image at the start point of the drag operation (step S803). FIG. 17 is a diagram illustrating a method for calculating the amount of change in the first threshold. An image 1900 is an example of a medical image presented to the user. An image 1901 is a probability image corresponding to the image 1900. A graph 1903 indicates a curve 1906 obtained by plotting probability values on a segment 1902 in the image 1901. In the graph 1903, a vertical axis represents a probability value, and a horizontal axis represents a position on the segment 1902.

In FIG. 17, a point E100 indicates a position at which the segment 1902 and a boundary line of a candidate area 1907 intersect. A point E110 indicates a position at which the segment 1902 and an inner boundary line of a modification area 1908 intersect, and a point E120 indicates a position at which the segment 1902 and an outer boundary line of the modification area 1908 intersect.

In the example illustrated in FIG. 17, the point E100 is input as a start point 1904 of a drag operation, which has been performed rightward along the segment 1902 by an amount of movement 1905. The amount of movement 1905 is in a direction of a normal line of an isopleth at the start point 1904.

The lesion area specification unit 105 receives operation information regarding the drag operation from the input unit 104 and calculates a product of a predetermined coefficient, a reciprocal of the inclination of the probability image at the start point 1904, and the amount of movement 1905 in the drag operation as the amount of change in the first threshold.

More specifically, the lesion area specification unit 105 may calculate an amount of change 1910 in the first threshold such that, as represented by the following expression (3), the amount of change 1910 in the first threshold becomes proportional to the amount of movement 1905 in the drag operation and inversely proportional to the inclination of the probability image at the start point 1904.

Amount of change in first threshold=Coefficient×
(Amount of movement in drag operation/Inclination at start point of drag operation) (3)

The coefficient may be, for example, 1.

The method for calculating the amount of change 1910 is not limited to this. For example, an upper limit and a lower limit may be provided for the amount of change, instead. The upper limit indicates a maximum value of the amount of change 1910 at a time when a drag operation is performed in a direction in which the candidate area 1907 is enlarged, and the lower limit indicates a minimum value of the amount of change 1910 at a time when a drag operation is performed in a direction in which the candidate area 1907 is reduced.

An upper limit and a lower limit may also be provided for the inclination at the start point 1904. In this case, if the inclination at the start point 1904 is larger than the upper limit, the inclination is set to the upper limit, and the amount of change 1910 is calculated. If the inclination at the start point 1904 is smaller than the lower limit, the inclination is set to the lower limit, and the amount of change 1910 is calculated.

In FIG. 15, the lesion area specification unit 105 modifies, in step S804, the candidate area and determines a lesion area by updating the first threshold using the amount of change in the first threshold calculated in step S803 (step S804).

As illustrated in FIG. 17, the lesion area specification unit 105 may calculate a probability value V1' by subtracting the amount of change 1910 from a probability value V1 at the start point 1904 and set an isopleth of the probability value V1' passing through a point E100' on the curve 1906 corresponding to the probability value V1' as a new boundary line. As a result, the boundary line of the candidate area 1907 is expanded from the point E100 to the point E100'.

Since, in the above example, the drag operation is performed rightward from the start point 1904, that is, in a direction in which the candidate area 1907 is enlarged, the amount of change 1910 is subtracted from the probability value V1 at the start point 1904. If a drag operation is performed leftward from the start point 1904, that is, in a direction in which the candidate area 1907 is reduced, on the other hand, a value obtained by adding the amount of change 1910 to the probability value V1 at the start point 1904 is calculated as the probability value V1', and a new boundary line is set.

The lesion area specification unit 105 may calculate the modified candidate area 1907 and display the modified candidate area 1907 on the display through the output unit 103 after the drag operation ends or during the drag operation. A start point of a drag operation is not limited to a point on the boundary line of the candidate area 1907. A start point of a drag operation may be any point inside the candidate area 1907 or any point in a certain area including the boundary line of the candidate area 1907.

By performing steps S801 to S804, a lesion area is determined in step S104.

If the candidate area need not be modified, the process ends while skipping steps S801 to S804. In addition, if the candidate area need not be modified, the user may input an operation indicating that the candidate area need not be modified in order to skip steps S801 to S804. In addition, if an operation for modifying the candidate area is performed a plurality of times, steps S801 to S804 may be performed a plurality of times.

Figure 18:
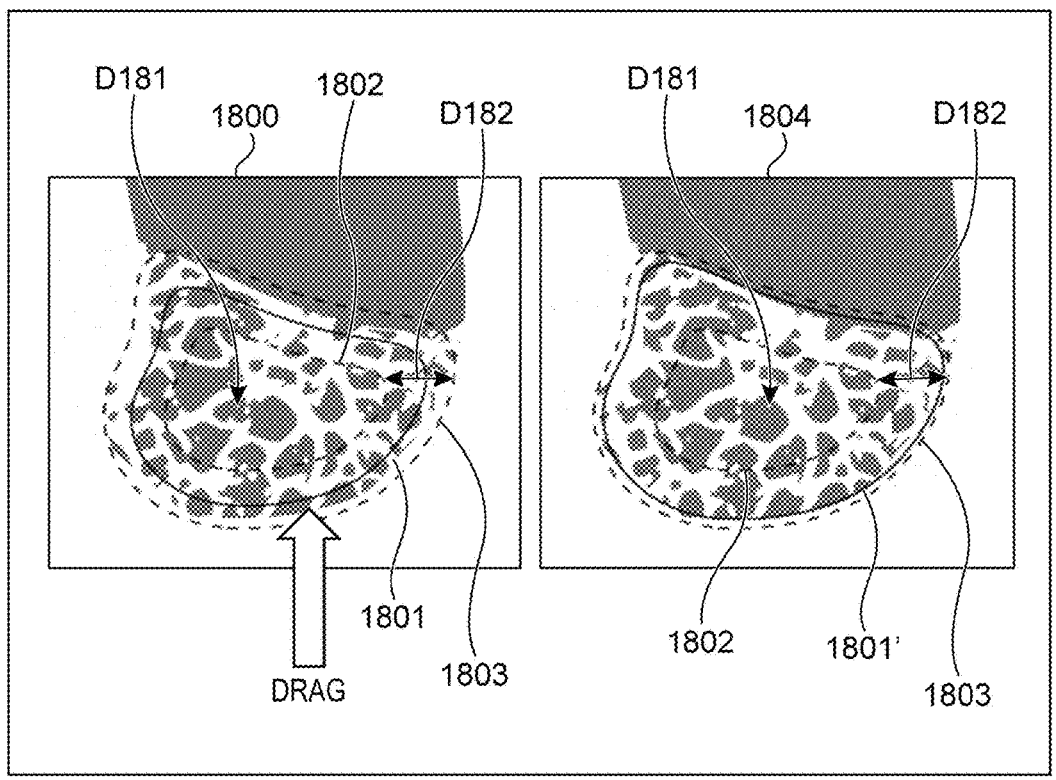
FIG. 18 is a diagram illustrating modification of a candidate area according to the second embodiment of the present disclosure.

FIG. 18 is a diagram illustrating modification of a candidate area according to the second embodiment of the present disclosure. An image 1800 indicates a candidate area before modification and a modification area, and an image 1801 indicates a modified candidate area and the modification area.

In FIG. 18, a boundary line 1801 is a boundary line of a candidate area D181, a boundary line 1802 is an inner boundary line of a modification area D182, and a boundary line 1803 is an outer boundary line of the modification area D182.

In the image 1800, a drag operation for moving the boundary line 1801 to the outside and enlarging the candidate area D181 is performed. As a result, the lesion area specification unit 105 calculates the amount of change in the first threshold in accordance with the amount of movement in the drag operation and an inclination at a start point of the drag operation using expression (3). In this case, since the drag operation for enlarging the candidate area D181 has been performed, a boundary line 1801' is expanded from the boundary line 1801 by a value according to the amount of change in the first threshold as indicated in an image 1804. That is, the lesion area specification unit 105 sets a value obtained by subtracting the amount of change in the first threshold from the current first threshold as a new first threshold and an isopleth of the first threshold as the boundary line 1801' of the modified candidate area D181.

If a drag operation for moving the boundary line 1801 inward is performed to reduce the candidate area D181, the lesion area specification unit 105 sets a value obtained by adding the amount of change in the first threshold to the current first threshold as a new first threshold and the isopleth of the first threshold as the boundary line 1801' of the modified candidate area D181.

If an operation for confirming a lesion area is not performed in step S804, the process returns to step S102 illustrated in FIG. 2, and steps S102 to S104 may be repeated.

In the second embodiment, too, a specification target image including a texture lesion is to be processed, a reason of which is the same as in the first embodiment.

As described above, the information terminal 100 according to the present embodiment modifies a boundary line of a candidate area in accordance with a drag operation performed by the user. At this time, the candidate area is modified such that the amount of change in the first threshold, that is, the amount of change in the boundary line, becomes smaller as an inclination of probability values at a start point of the drag operation becomes larger. In an area in which an inclination of probability values is large, a boundary line of a candidate area might not fit inside a boundary line of an actual lesion area or might be positioned inside the lesion area even with a slight drag operation, a drag operation needs to be performed carefully. In an area in which an inclination of probability values is small, on the other hand, a drag operation need not be performed as carefully as in an area in which an inclination of probability values is large. In the present embodiment, therefore, the amount of change in the first threshold is calculated such that the amount of change in the first threshold becomes proportional to the amount of movement in a drag operation and inversely proportional to an inclination of a probability image at the start point 1904. As a result, the user can finely adjust a boundary line of a candidate area in an area in which an inclination is large, where a careful drag operation is required, and the boundary line of the candidate area can be modified simply and accurately. In an area in which an inclination is small, where a careful drag operation is not required, on the other hand, the user can roughly adjust a candidate area and promptly determine the candidate area.

Although the information terminal 100 in the present disclosure has been described on the basis of the above embodiments, the present disclosure is not limited to these embodiments. The present disclosure also includes modes obtained by modifying the above embodiments in various ways conceivable by those skilled in the art and modes constructed by combining components from different embodiments insofar as the scope of the present disclosure is not deviated from.

The information terminal 100 may be specifically configured as a computer system including a microprocessor, a ROM, a RAM, a hard disk drive, a display unit, a keyboard, and a mouse. The RAM or the hard disk drive stores a computer program. The microprocessor operates in accordance with the computer program, and the information terminal 100 achieves functions thereof. The computer program is configured by combining a plurality of command codes indicating instructions to a computer in order to achieve the certain functions.

Furthermore, some or all of the components of each of the above control methods may be configured by a single system large-scale integration (LSI) circuit. A system LSI circuit is an ultra-multifunctional LSI circuit fabricated by integrating a plurality of components on a single chip and, more specifically, a computer system configured by including a microprocessor, a ROM, and a RAM. The RAM stores a computer program. The microprocessor operates in accordance with a computer program, and the system LSI circuit achieves functions thereof.

Furthermore, some or all of the components of each of the above control methods may be configured by an integrated circuit (IC) card or a separate module removably attached to the control method. The IC card or the module is a computer system including a microprocessor, a ROM, and a RAM. The IC card or the module may include the ultra-multifunctional LSI circuit. The microprocessor operates in accordance with a computer program, and the IC card or the module achieves functions thereof. The IC card or the module may be tamper-resistant.

In addition, the information terminal 100 in the present disclosure may be achieved by one of the control methods described in the above embodiments. The control methods may each be configured by a computer program executed by a computer or a digital signal including the computer program.

Furthermore, the computer program or the digital signal may be stored in a computer-readable non-transitory recording medium such as a flexible disk, a hard disk, a CD-ROM, a magneto-optical (MO) disk, a digital versatile disc (DVD), a DVD-ROM, a DVD-RAM, a Blu-ray Disc (BD; registered trademark), or a semiconductor memory. The present disclosure may be configured by the digital signal stored in one of these non-transitory recording media.

In addition, the present disclosure may be the computer program or the digital signal transmitted through an electrical communication line, a wireless or wired communication line, a network typified by the Internet, or datacasting.

In addition, the present disclosure may be a computer system including a microprocessor and a memory. The memory may store the computer program, and the microprocessor may operate in accordance with the computer program.

In addition, the program or the digital signal may be executed by another independent computer system after being stored in one of the above non-transitory recording media and transported or transported through the network.

Since a lesion area can be efficiently determined in the present disclosure, the present disclosure is effective in making diagnoses using medical images.

What is claimed is:

1. A method for controlling an information terminal including a display, the information terminal being connected to a case retrieval system that retrieves a medical image by referring to a medical image database, the method comprising:
   (a) receiving a first medical image including a plurality of pixels;
   (b) calculating, if a lesion included in the first medical image is a texture lesion, a probability value indicating a probability that each of the plurality of pixels of the first medical image is included in a lesion area by inputting a pixel value of the pixel and pixel values of surrounding pixels of the pixel to an identification device for identifying a predetermined lesion area indicating the texture lesion, the texture lesion being a lesion including one of a plurality of particular shadow patterns;
   (c) displaying, on the display, a second medical image obtained by superimposing a candidate area and a modification area of the candidate area upon the first medical image, the candidate area being determined on the basis of a pixel whose probability value is larger than a first threshold among the plurality of pixels, the modification area being determined on the basis of a pixel whose probability value is within a probability range among the plurality of pixels, the probability range including the first threshold;
   (d) detecting an input from a user on the second medical image displayed on the display; and
   (e) displaying a third medical image obtained by superimposing the lesion area upon the first medical image, the lesion area being determined by modifying the candidate area on the basis of the input from the user and the modification area.

2. The method according to claim 1,
wherein, in (c), the modification area to be superimposed upon the second medical image is divided into a plurality of sub-areas, and
wherein, in each of the plurality of sub-areas, a longest straight line connecting two pixels selected from the sub-area is equal to or shorter than a second threshold.

3. The method according to claim 2,
wherein, in (d), an input from the user as to whether to add or exclude each of the plurality of sub-areas to or from the candidate area is detected, and
wherein, in (e), a candidate area determined on the basis of the input from the user is displayed as the lesion area.

4. The method according to claim 1,
wherein, in (c), the modification area is displayed such that the modification area includes the candidate area,
wherein, in (d), an input from the user on a pixel included in the modification area is detected, and
wherein, in (e), the lesion area is an area obtained by enlarging or reducing the candidate area on the basis of a part of the modification area in accordance with the input from the user.

5. The method according to claim 4,
wherein, in (e), a degree to which the candidate area is enlarged or reduced when an input from the user on a first pixel has been detected is set lower than when an input from the user on a second pixel has been detected, and
wherein an inclination of probability values of surrounding pixels of the first pixel is larger than an inclination of probability values of surrounding pixels of the second pixel.

6. The method according to claim 5,
wherein, in (d), a drag operation performed by the user is detected as the input, and
wherein, in (e), the first and second pixels are each a pixel at a start point of the drag operation, and the degree to which the candidate area is enlarged or reduced is proportional to an amount of movement in the drag operation and inversely proportional to the inclination.

7. An information terminal including a display, the information terminal being connected to a case retrieval system that retrieves a medical image by referring to a medical image database, the information terminal comprising:
   a probability image calculator that receives a first medical image including a plurality of pixels and, if a lesion included in the first medical image is a texture lesion including one of a plurality of particular shadow patterns, calculates a probability value included in a lesion area by inputting a pixel value of each of the plurality of pixels of the first medical image and pixel values of surrounding pixels of the pixel to an identification device for identifying a predetermined lesion area;
   an outputter that determines, for the first medical image, a candidate area on the basis of a pixel whose probability value is equal to or larger than a first threshold among the plurality of pixels and a modification area of the candidate area on the basis of a pixel whose probability value is within a probability range including the first threshold among the plurality of pixels, superimposes the candidate area and the modification area upon the first medical image, and displays a second medical image on the display;
   an inputter that detects an input from a user on the second medical image displayed on the display; and
   a lesion area specifier that specifies a lesion area by modifying the candidate area on the basis of the input from the user detected by the inputter and the modification area,
wherein the outputter displays, on the display, a third medical image upon which the lesion area is superimposed.

8. The information terminal according to claim 7,
wherein the probability image calculator divides the modification area to be superimposed upon the second medical image into a plurality of sub-areas, and
wherein, in each of the plurality of sub-areas, a longest straight line connecting two pixels selected from the sub-area is equal to or shorter than a second threshold.

9. The information terminal according to claim 8,
wherein the inputter detects an input from the user as to whether to add or exclude each of the plurality of sub-areas to or from the candidate area, and wherein the lesion area specifier displays a candidate area determined on the basis of the input from the user as the lesion area.

10. The information terminal according to claim 9, wherein the outputter displays the modification area such that the modification area includes the candidate area,
wherein the inputter detects an input from the user on a pixel included in the modification area, and
wherein the lesion area specifier determines the lesion area by enlarging or reducing the candidate area on the basis of a part of the modification area in accordance with the input from the user.

11. The information terminal according to claim 10, wherein the lesion area specifier sets a degree to which the candidate area is enlarged or reduced when an input from the user on a first pixel has been detected lower than when an input from the user on a second pixel has been detected, and
wherein an inclination of probability values of surrounding pixels of the first pixel is larger than an inclination of probability values of surrounding pixels of the second pixel.

12. The information terminal according to claim 11, wherein the inputter detects a drag operation performed by the user as the input, and
wherein the first and second pixels are each a pixel at a start point of the drag operation, and the degree to which the candidate area is enlarged or reduced is proportional to an amount of movement in the drag operation and inversely proportional to the inclination.

13. A recording medium storing a control program for causing a device including a processor connected to a case retrieval system that retrieves a medical image by referring to a medical image database to perform a process, the process comprising:
receiving a first medical image including a plurality of pixels;
calculating, if a lesion included in the first medical image is a texture lesion including one of a plurality of particular shadow patterns, a probability value indicating a probability that each of the plurality of pixels of the first medical image is included in a lesion area by inputting a pixel value of the pixel and pixel values of surrounding pixels of the pixel to an identification device for identifying a predetermined lesion area;
determining, for the first medical image, a candidate area on the basis of a pixel whose probability value is equal to or larger than a first threshold among the plurality of pixels and a modification area of the candidate area on the basis of a pixel whose probability value is within a probability range including the first threshold among the plurality of pixels, superimposing the candidate area and the modification area upon the first medical image, and displaying a second medical image on a display;
detecting an input from a user on the second medical image displayed on the display;
specifying a lesion area by modifying the candidate area on the basis of the detected input from the user and the modification area; and
displaying, on the display, a third medical image upon which the lesion area is superimposed.

14. A determination method comprising:
receiving a medical image including pixels, each of the pixels having a pixel value;
calculating probability values each corresponding to the pixels, each of the probability values indicating a probability that a corresponding pixel is included in a lesion area;
determining, from among a first area, a second area, a third area, and a fourth area, an area to which each of the pixels belongs, each of pixels included in the first area having a pixel value equal to or larger than an upper limit, each of pixels included in the second area having a pixel value equal to or larger than a first threshold but smaller than the upper limit, each of pixels included in the third area having a pixel value larger than a lower limit but smaller than the first threshold, each of pixels included in the fourth area having a pixel value equal to or smaller than the lower limit, the upper limit being larger than the first threshold, the first threshold being larger than the lower limit;
receiving first selections of one or more areas included in the second area;
determining one or more fifth areas being included in the second area and not being selected in the first selections;
receiving second selections of one or more areas included in the third area;
determining one or more sixth areas being included in the third area and being selected in the second selections; and
determining pixels included in the first area, the one or more fifth areas, and the one or more sixth areas are included in the lesion area.

* * * * *